US007879547B2

(12) United States Patent
Rothenberg et al.

(10) Patent No.: US 7,879,547 B2
(45) Date of Patent: Feb. 1, 2011

(54) METHOD OF DETECTING THE PRESENCE OF ASTHMA OR ALLERGIES IN A PATIENT

(75) Inventors: Marc E. Rothenberg, Cincinnati, OH (US); Nives Zimmermann, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 415 days.

(21) Appl. No.: 11/735,954

(22) Filed: Apr. 16, 2007

(65) Prior Publication Data

US 2007/0190567 A1 Aug. 16, 2007

Related U.S. Application Data

(62) Division of application No. 10/377,998, filed on Feb. 28, 2003, now abandoned.

(60) Provisional application No. 60/361,606, filed on Mar. 1, 2002.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| 5,854,289 A | 12/1998 | Bianchi et al. |
| 6,376,169 B1 | 4/2002 | Adams et al. |
| 2002/0019405 A1 | 2/2002 | Garvey et al. |

FOREIGN PATENT DOCUMENTS

WO   WO 00/67754 A   11/2000

OTHER PUBLICATIONS

Zimmermann et al., J. Clin. Invest. 111: 1863-1874, 2003.*
The International Search Report from PCT/US03/06183 dated Jan. 28, 2005.
Black, et al., *A metalloproteinase disintegrin that releases tumour-necrosis factor-α from cells*, Nature, Vo. 385, 1997 pp. 729-733.
Bradding, et al., *15-Lipoxygenase Immunoreactivity in Normal and in Asthmatic Airways*, Am J Respir Crit Care Med., vol. 151, pp. 1201-1204, 1995.
Cabral, et al., *Structural Organization and Regulation of the Small Proline-rich Family of Cornified Envelope Precursors Suggest a Role in Adaptive Barrier Function*, The Journal of Biological Chemistry, vol. 26, No. 22, Jun. 1, 2001, pp. 19231-19237.
Colleluori, et al., *Classical and Slow-Binding Inhibitors of Human Type II Arginase*, Biochemistry, 2001, 9356-9362, 40, Department of Biochemistry, Temple University School of Medicine, Philadelphia, Pennsylvania.
Hakonarson, et al., *Current concepts on the genetics of asthma*, Curr Opin Pediatr 2001, 13:267-277.

Heller-Milev, et al., *Expression of small proline rich proteins in neoplastic and inflammatory skin diseases*, British Journal of Dermatology 2000;143:733-740.
Holgate, et al., *Genetic and environmental interaction in allergy and asthma*, J Allergy Clin Immunol Dec. 1999; pp. 1139-1146.
Huang, et al., *Molecular and Biological Characterization of the Murine Leukotriene $B_4$ Receptor Expressed on Eosinophils*, J. Exp. Med., vol. 188, No. 6, Sep. 21, 1998, pp. 1063-1074.
Grünig, et al., *Requirement for IL-13 Independently of IL-4 in Experimental Asthma*, Science, vol. 282, Dec. 18, 1998, pp. 2261-2263.
Kawasaki, et al., *Intervention of Thymus and Activation-Regulated Chemokine Attenuates the Development of Allergic Airway Inflammation and Hyperresponsiveness in Mice[1]*, Journal of Immunology, 2001, vol. 166 pp. 2055-2062.
Kuitert, et al., *Eicosanoid mediator expression in mononuclear and polymorphonuclear cells in normal subjects and patients with atopic asthma and cystic fibrosis*, Thorax, 1996:51:1223-1228.
Lloyd, et al., *CC Chemokine Receptor (CCR)3/Eotaxin Is Followed by CCR4/Monocyte-derived Chemokine in Mediating Pulmonary T Helper Lymphocyte Type 2 Recruitment after Serial Antigen Challenge* In Vivo, J. Exp. Med., vol. 191, No. 2, Jan. 17, 2000, pp. 265-273.
MacLeod, et al., *$y^+$-type Cationic Amino Acid Transport: Expression and Regulation of the mCat Genes*, J. Exp. Biol. 196:109-121 (1994).
Meurs, et al., *Modulation of Cholinergic Airwar Reactivity and Nitric Oxide Production by Eendogenous Arginase Activity*, British Journal of Pharmacology, 2000, 1973-1798, 130, Macmillan Publishers Ltd.
Meyskens, Jr., et al., *Development of Difluoromethylornithine (DFMO) as a Chemoprevention Agent*, Clinical Cancer Research, vol. 5:945-951, May 1999.
Mills, Charles D., *Macrophage Arginine Metabolism to Ornithine/Urea or Nitric Oxide/Citrulline: A Life or Death Issue*, Critical Reviews in Immunology, 21(4):399-426, 2001.
Morris, Sidney M., Jr., *Regulation of Enzymes of the Urea Cycle and Arginine Metabolism*, Annu. Rev. Nutr. 2002, 22:87-105.
Munder, et al., *Th1/Th2-Regulated Expression of Arginase Isoforms in Murine Macrophages and Dendritic Cells*, The Journal of Immunology, 1999, 163:3771-3777.
Nicholson, et al., *Sustained Nitric Oxide Production in Macrophages Requires the Arginine Transporter CAT2*, The Journal of Biological Chemistry, vol. 276, No. 19, May 11, 2001, pp. 15881-15885.

(Continued)

*Primary Examiner* — Robert Landsman
*Assistant Examiner* — Gyan Chandra
(74) *Attorney, Agent, or Firm* — Knobbe Martens Olson & Bear LLP

(57) ABSTRACT

Several genes are upregulated in the lung of asthma or allergy sufferers. Many of the genes up-regulated in asthma are involved in arginine metabolism in the lung. Moreover, a set of 291 signature genes was found that can be used to indicate a patient's predilection for developing asthma or the patient's degree of suffering. Also, a set of 59 signature genes were found that indicate a patient's predilection for developing allergies. Many of the up-regulated genes relating to asthma were from the arginine metabolic pathway. Other genes, such as ADAM8, SPRR2A and SPRR2B were also strongly upregulated in asthma. Treatment of asthma may be accomplished by administering compositions which decrease the levels of Arginase I, Arginase II, CAT2, or other arginase pathway members in the lung. Additionally, detection of altered levels of these proteins or the mRNA encoding them may be useful to diagnose the presence of asthma in a patient.

19 Claims, 16 Drawing Sheets

OTHER PUBLICATIONS

Prakash, et al., *Effect of α-Difluoromethylornithine, an Enzyme-activated Irreversible Inhibitor of Ornithine Decarboxylase, on L1210 Leukemia in Mice*, Cancer Research 38, 3059-3062 (1978).

Que, et al., *Effects of Arginase Isoforms on NO Production by Nnos*, Nitric Oxide: Biology and Chemistry, vol. 6, No. 1, pp. 1-8, 2002.

Rankin, et al., *Phenotypic and physiologic characterization of transgenic mice expressing interleukin 4 in the lung: Lymphocytic and eosinophilic inflammation without airway hyperreactivity*, Proc. Natl. Acad. Sci. USA vol. 93, pp. 7821-7825, Jul. 1996.

Rutschman, et al., *Cutting Edge: Stat6-Dependent Substrate Depletion Regulates Nitric Oxide Production*, The Journal of Immunology, 2001, 166:2173-2177.

Rothenberg, et al., *Targeted Disruption of the Chemokine Eotaxin Partially Reduces Antigen-induced Tissue Eosinophilia*, J. Exp. Med. vol. 185, No. 4, Feb. 17, 1997, pp. 785-790.

Schlomann, et al., *The Metalloprotease Disintegrin ADAM8*, The Journal of Biological Chemistry, vol. 277, No. 50, Dec. 13, 2002, pp. 48210-48219.

Sigal, et al., *Human 15-lipoxygenase:induction by Interleukin-4 and insights into positional specificity*, Journal of Lipid Mediators, 6 (1993) 75-88.

Tesfaigzi, et al., *Expression, Regulation, and Function of the SPR Family of Proteins*, Cell Biochemistry and Biophysics, Vo. 30, 1999 pp. 243-265.

Wei, et al., *IL-4 and IL-13 upregulate arginase I expression by cAMP and JAK/STAT6 pathways in vascular smooth muscle cells*, Am J Physiol Cell Physiol 279:C248-C256, 2000.

Wills-Karp, Marsha, *IL-12/IL-13 axis in allergic asthma*, J Allergy Clin Immunol 2001;107:9-18.

Yang, et al., *Interleukin-13 Mediates Airways Hyperreactivity through the IL-4 Receptor-Alpha Chain and STAT-6 Independently of IL-5 and Eotaxin*, Am. J. Respir. Cell Mol. Biol. vol. 25, pp. 522-530, 2001.

Zimmermann, et al., *Gene Expression Profile Analysis in Experimental Asthma*, Abstract, The Journal of Allergy and Clinical Immunology, Jan. 2002, Part 2, vol. 109, No. 1.

\* cited by examiner

METHOD OF DETECTING THE PRESENCE OF ASTHMA OR ALLERGIES IN A PATIENT

RELATED APPLICATIONS

This application is a divisional of U.S. patent application Ser. No. 10/377,998, filed Feb. 28, 2003, which claims priority to U.S. Provisional Application No. 60/361,606, filed Mar. 1, 2002. The contents of these applications are incorporated herein by reference in their entireties.

GOVERNMENTAL INTEREST

This invention was made with government support under grant number RO1 AI042242-04 from the National Institutes of Health/National Institute of Allergy and Infectious Diseases. The government has certain rights in the invention.

BACKGROUND OF THE INVENTION

1. Field of the Invention

Embodiments of the present invention relate generally to compositions and methods designed to aid in the treatment or detection of asthma or allergies.

2. Description of the Related Art

Asthma, a chronic disorder which causes detrimental, and in some cases, potentially fatal pulmonary inflammation affects 15 million Americans and accounts for approximately 12.7 billion dollars in health care costs each year. Despite extensive ongoing research, asthma is currently on the rise. The inability of researchers to develop an effective treatment for asthma is largely due to the complexity of the disease. Discovering effective treatments with broad applicability is extremely difficult because asthma derives from a wide number of factors. For example, multiple specific inflammatory pathways, many of which are poorly understood, are thought to interplay with one another to produce the symptoms that result in a diagnosis of asthma in a patient. In addition, research is further complicated by the fact that the relative importance of those pathways can differ between individual asthma sufferers.

Experimentation in the asthma field has largely focused on analysis of the cellular and molecular events induced by allergen exposure in sensitized animals (primarily mice) and humans. These studies have identified elevated production of IgE, mucus hypersecretion, airways obstruction, inflammation and enhanced bronchial reactivity to spasmogens in the asthmatic response. Clinical and experimental investigations have demonstrated a strong correlation between the presence of $CD4^+T$ helper 2 lymphocytes (Th2 cells) and disease severity suggesting an integral role for these cells in the pathophysiology of asthma. Th2 cells are thought to induce asthma through the secretion of an array of cytokines that activate inflammatory and residential effector pathways both directly and indirectly. In particular, interleukin-4 (IL-4) and interleukin-13 (IL-13) are produced at elevated levels in the asthmatic lung and are thought to be central regulators of many of the hallmark features of disease.

Arginine Metabolism

L-arginine is a semi-essential basic amino acid that is involved in two biochemical pathways, the citrulline-nitric oxide (NO) cycle and the urea cycle as illustrated in FIG. 1. The bulk of the urea cycle occurs in the liver, the main organ containing the full enzymatic machinery necessary for the urea cycle. The enzyme arginase is the only urea cycle enzyme that exists in two isoforms (60% amino acid homology), which are encoded by different genes on distinct chromosomes, designated type I and type II. Arginase I is a cytoplasmic protein that is primarily expressed in the liver; whereas arginase II is a mitochondrial protein expressed in a variety of tissues, especially the kidney and prostate. The downstream enzymes ornithine decarboxylase (ODC) and L-ornithine amino transferase (OAT) are specifically expressed in the cytoplasm and mitochondria, respectively, suggesting coordinated biochemical links for the two isoenzymes.

Arginase I deficiency in humans results in hyperargininemia and a progressive neurological deterioration that is usually fatal. Whereas arginase I deficient transgenic mice die within 9-11 days after birth, arginase II deficient mice are grossly normal. One development in the past several years concerning L-arginine metabolism was the finding that arginase can be expressed in many tissues and cell types following exposure to a variety of cytokines and agents. Of the cytokines shown to regulate arginase, IL-4, IL-10, and IL-13 appear to be the most potent, especially in macrophages. Although both arginases are inducible by various stimuli in vitro, arginase I appears to be more strongly induced by Th2 cytokines. However, this has not been extensively studied in cell types other than macrophages.

The exact function of arginase in extrahepatic tissue is not well understood. However, the product of arginase, L-ornithine, is a precursor in the production of polyamines (e.g. putrescine, spermidine, and spermine) and proline, which control cell proliferation and collagen production, respectively. In fact, increased expression of arginase I alone is sufficient to result in increased proliferation rates of vascular smooth muscle and endothelial cells. Thus, arginase activity is potentially critically linked to cell growth and connective tissue production, notably, both of these processes are hallmark pathological features of chronic asthma and allergies (FIG. 1).

In addition to being metabolized to L-ornithine, L-arginine is also a precursor of NO, a free radical molecule involved in a wide range of biological processes. NO is formed from L-arginine by the enzyme NOS. Three isoforms of NOS have been described. NOS1 and NOS3 are constitutively expressed and their activity is calcium dependent. NOS1 is expressed in neurons and is thought to have a role in neurotransmission, whereas NOS3, or endothelial NOS, has a role in smooth muscle relaxation and bronchodilation. NOS2, inducible NOS (iNOS), is calcium-independent, and is up-regulated in response to inflammatory mediators such as endotoxin and interferon-γ, leading to the production of large amounts of NO.

The diagram in FIG. 1 illustrates the role of cationic amino acid transporter-2 (CAT2) in the arginase pathway. Extracellular L-arginine is required for sustained NO and L-ornithine generation from L-arginine, implicating an important role for L-arginine transport through the plasma membrane. Among the several transport systems that mediate L-arginine uptake, system $y^+$ is widely expressed and considered the major L-arginine transporter in most cells and tissues. Encoded by cationic amino acid transporters CAT1, CAT2, and CAT3, system $y^+$ is a $Na^+$-independent high affinity cationic amino acid transport system. With the exception of the liver, CAT1 is expressed virtually ubiquitously and is required for viability, whereas CAT2 is expressed in a more restricted number of tissues; CAT3 is primarily expressed in the brain.

Due to differential splicing of two exons, CAT2 mRNA exists in two isoforms: CAT2A, a low affinity transporter that is expressed primarily in the liver, and the high affinity CAT2 (CAT2B). CAT1 and -2 are homologous proteins that lack a signal peptide but contain 12 transmembrane spanning domains with an intracellular amino-terminus. Interestingly, CAT2 was originally cloned from lymphoma cell line cDNA and was named Tea (T cell early activation factor), because it is induced early in the response of normal T cells to mitogens. However, the role of CAT2 in T cell immune responses has not yet been reported but preliminary studies have indicated an important role for this molecule in experimental autoimmune encephalitis. The first indication that CAT2 may be involved in critically regulating substrate availability for iNOS or arginase was the finding that pro-inflammatory molecules (e.g. lipopolysaccharide [LPS]) regulate CAT2 expression. In contrast, cat-1 is a "housekeeping" gene that is not induced under conditions that induce CAT2. A further interesting relationship has been established by the finding that eosinophil cationic proteins inhibit L-arginine uptake by macrophages. Recent analysis of CAT2-deficient mice has revealed that sustained NO production in macrophages requires CAT2. The 95% decrease in L-arginine uptake by CAT2 deficient macrophages, indicates that CAT2 is the major L-arginine transporter in macrophages.

CAT2 was originally cloned from lymphoma cell line cDNA and was named Tea (T cell early activation factor), because it was induced early in the response of normal T cells to mitogens. (MacLeod et al., *J Exp Biol*, 196:109-21 (1994)). However, previous studies on the role of CAT2 in immune responses have been primarily limited to its effects on NO production (Nicholson et al., *J Biol Chem*, 276:15881-5 (2001)). It was thus important to further characterize exactly which CAT2 isoform is expressed in the asthmatic lung. CAT2 is expressed as two separate isoforms depending upon the specific utilization of exon 7 (Type 2B) or exon 8 (Type 2A) (Nicholson et al., *J Biol Chem*, 276:15881-5 (2001)). CAT2A has a lower affinity for L-arginine and is thought to be mainly expressed in the liver (MacLeod et al., *J Exp Biol*, 196:109-21 (1994)).

Because incidence of asthma and allergies are on the rise, research leading to a better understanding and treatment of this disease is needed. Thus, what is needed in the art are new methods of treating an individual suffering from asthma or allergies, new methods for detecting individuals at risk for asthma or allergies, and new methods for phenotyping patients (e.g. predicting their prognosis and response to treatment).

SUMMARY OF THE INVENTION

One embodiment of the invention is a method of treating asthma or allergies in a patient, that includes: identifying an individual in need of treatment for asthma or allergies; and administering a molecule that is capable of decreasing the production of a protein involved in arginine metabolism.

Another embodiment is a method of detecting the presence of asthma or allergies in a patient that includes: measuring the levels a product produced from at least one gene involved in arginine metabolism from the patient; measuring genetic variabilities (in expression or gene sequence) from a product produced from at least one gene involved in arginine metabolism; and comparing the measurement to measurements obtained from control individuals, wherein a patient exhibiting higher levels of the at least one gene as compared to the control individuals is determined to have asthma or allergies.

Yet another embodiment is a therapeutic composition for the treatment of asthma or allergies that includes an arginase inhibitor in a pharmaceutically acceptable carrier.

Still another embodiment is a therapeutic composition for the treatment of asthma or allergies, comprising an inhibitor of CAT2 activity in a pharmaceutically acceptable carrier.

One additional embodiment is a method of identifying individuals at risk for asthma or allergies that includes: identifying an individual who does not yet exhibit symptoms of asthma or allergy, measuring the levels of a product produced from a gene in the arginase pathway; and comparing the levels of product to measurements obtained from control individuals, wherein a patient exhibiting elevated levels of the product is determined to be at risk for asthma or allergies.

Another embodiment is a method of treating asthma or allergies in a patient that includes: identifying an individual in need of treatment for asthma or allergies; and administering a molecule that is capable of decreasing activity of ADAM8 protein in the patient.

An additional embodiment is a method of treating asthma or allergies in a patient by identifying an individual in need of treatment for asthma or allergies; and administering a molecule that is capable of decreasing activity of SPRR2A, SPRR2B or related SPRR family member proteins in the patient.

One other embodiment is a method of determining a patient's risk for developing asthma that includes: providing a biological sample from the patient; and determining the expression level in the biological sample of a subset of the genes shown in Table 1, wherein an increased level of expression of the subset of the genes in comparison to a control biological sample is indicative that the patient has an increased risk for developing asthma.

Yet another embodiment is a method of determining a patient's risk for developing allergies by: providing a biological sample from the patient; and determining the expression level in the biological sample of a subset of the genes shown in Table 2, wherein an increased level of expression of the subset of the genes in comparison to a control biological sample is indicative that the patient has an increased risk for developing allergies.

One other embodiment is a method of discovering a compound that is effective for treating asthma or allergies that includes: providing a candidate compound; determining whether the compound inhibits arginine metabolism, wherein inhibition of arginine metabolism is indicative that the compound is effective for treating asthma or allergies.

BRIEF DESCRIPTION OF THE DRAWINGS

FIG. 8 illustrates the regulation of arginase by IL-13 and STAT6.

FIG. 11A illustrates in vitro treatment of lung lysates from ovalbumin challenged mice with NOHA. FIG. 11B illustrates in vitro treatment of transgenic mice that overexpress interleukin 4 with NOHA.

DETAILED DESCRIPTION

Figure 1:
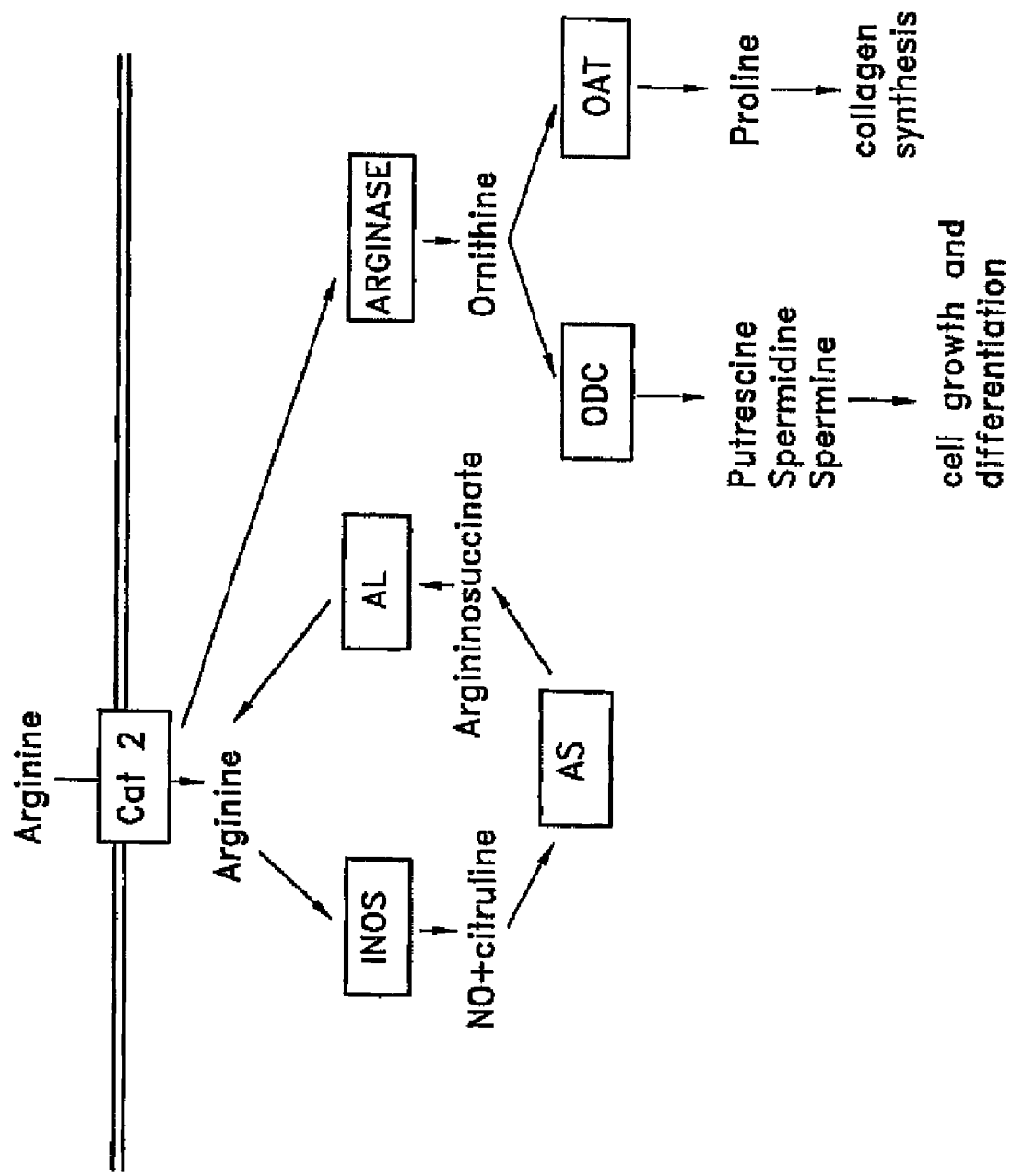
FIG. 1 provides a schematic of the arginine metabolism pathway.

Embodiments of the invention relate to the discovery of genes involved in asthma and allergy. Thus, one embodiment of the invention relates to the discovery of a set of 291 "signature" genes (Table 1) that were found to be consistently regulated in asthma models of disease. In addition, a subset of 59 genes (Table 2) were found to be consistently elevated in various allergic diseases irrespective of the tissue involved (lung vs. intestine), providing a generalized genetic "signature" of allergy. Accordingly, patients can be genotyped for expression or genetic variability in each of these signature genes to determine their risk for developing asthma or allergy. Moreover, patients suffering from asthma or allergies can be tested for expression of the signature genes in order to more accurately predict their prognosis and responses to treatment regimes. Additionally, each of the genes can be targeted for possible drug intervention/treatment of allergic disease.

While embodiments of the invention relate to determining a patient's risk for developing asthma or allergies by comparing the patient's expression level of asthma or allergy signature genes to the levels shown in Tables 1 and 2, an exact correlation is not required to be within the scope of the invention. For example, a determination that a patient only exhibits increased expression of some of the signature genes is still indicative of a patient's risk for developing allergies or asthma. Thus, a biological sample that is taken from a patient and is determined to have increased expression of, for example, 1, 5, 10, 20, 30, 40, 50, 60, 70, 80, 90, 95 or 100 percent of the signature genes may still be determined to be at risk for allergies or asthma. It is the combination of the gene expression pattern, along with the expression level of each gene, of the signature genes that indicates a person's risk for developing allergies or asthma. For this reason, the scope of the invention is not limited to determining a patient is at risk for asthma by matching expression levels of all 291 asthma signature genes. Similarly, it is not required to match the expression levels of all 59 allergy signature genes in order to determine that a patient is at risk for developing allergies. For similar reasons, it is not necessary for a patient's gene expression profile to exactly match the allergy signature genes, or asthma signature genes in order to predict an existing patient's prognosis or responses to treatment regimes.

In addition, embodiments of the invention relate to the discovery of the relationship between the pulmonary arginase pathway and asthma. The methods disclosed herein were used to elucidate the involvement of the arginase pathway in both experimental asthma and in human asthma. An increased level in expression of several important arginase metabolism genes, including those encoding CAT2, arginase I, and arginase II proteins was strongly associated with asthma and allergy. It was also discovered that arginase induction by IL-4/IL-13 signaling is not just a marker of allergic airway responses, but that arginase is involved in the pathogenesis of multiple aspects of asthma. Accordingly, modulation of these arginase pathway genes or their products can be used to devise therapeutic and diagnostic strategies for treating asthma or allergies.

Embodiments of the invention also relate to the discovery that significant arginine metabolism occurs by arginase, and that this process has important ramifications on the manifestations of asthma and related diseases. As such, the arginine metabolism pathway represents an important therapeutic intervention strategy for the treatment of all allergic lung diseases. Manipulating the arginase pathway by inhibiting arginase activity itself, or by inhibiting the action of other arginase pathway members, is anticipated to provide a useful asthma treatment. Additionally, manipulation of the pulmonary arginase pathway may be useful for preventing the onset of asthma. Also, analyzing the genes involved in arginine metabolism can be used to diagnose the presence of asthma or allergies by quantitating of the levels of asthma metabolism pathway enzymes or products.

Another embodiment of the invention relates to the discovery that one of the signature genes, ADAM8, was very strongly associated with asthma and allergies. Thus, embodiments of the invention include kits, systems, and methods for diagnosing asthma by determining the level of ADAM8 in a patient. In addition, a treatment for asthma or allergy by administration of a therapeutically effective amount of a compound that inhibits ADAM8 is anticipated. An example of one such compound is batimastat (BB-94) as described in Schlomann, et al., *J Biol Chem* 2002 December 13;277(50): 48210-9. Accordingly, an embodiment of the invention is the treatment of asthma or allergies by administering to a patient a therapeutically effective amount of batimastat.

Another embodiment of the invention relates to the discovery that the signature genes included a family of molecules not previously associated with asthma called small proline rich proteins (SPRR), specifically SPRR2A and SPRR2B. The SPRR protein family is known to be involved in the differentiation and growth of cornified skin epithelium (Tesfaigzi J. Carlson D M, *Cell Biochem Biophys* 1999;30(2):243-65, Expression, regulation, and function of the SPR family of proteins. A review).

SPRR2A AND SPRR2B were very strongly associated with asthma and allergies. In addition, wild type mice treated with IL-13, which is thought to be a central regulator of asthma, caused markedly increased levels of lung SPRR2 (data not shown).

Thus, embodiments of the invention include kits, systems, and methods for diagnosing asthma by determining the level and variabilities (genetic or protein levels) of SPRR proteins or genes in a patient. In addition, a treatment for asthma or allergy by administration of a compound that modulates SPRR protein function is anticipated.

The initial determination of the genes upregulated during asthma pathogenesis was shown by a microarray analysis procedure performed on mice treated with various types of allergens, as described below.

Microarray Analysis of Gene Expression from Animals Undergoing Experimental Asthma DNA microarray profile analysis of mice undergoing experimental asthma, as disclosed herein, has revealed unprecedented insight into the complex pathways involved in disease pathogenesis. The determination that asthmatic responses involve the dynamic expression of ~6% of the tested genome, indicates that a vast number of gene products contribute to disease pathogenesis. Allergic lung responses were found to involve both a common set of "asthma signature genes" as shown in Table 1, and also, unique gene transcript profiles depending upon the mode of disease induction. Multiple genes not previously implicated in asthma were identified, exemplified by the elucidation of a pathway involving metabolism of arginine via CAT2 and the arginase enzyme pathway.

Figure 2A:
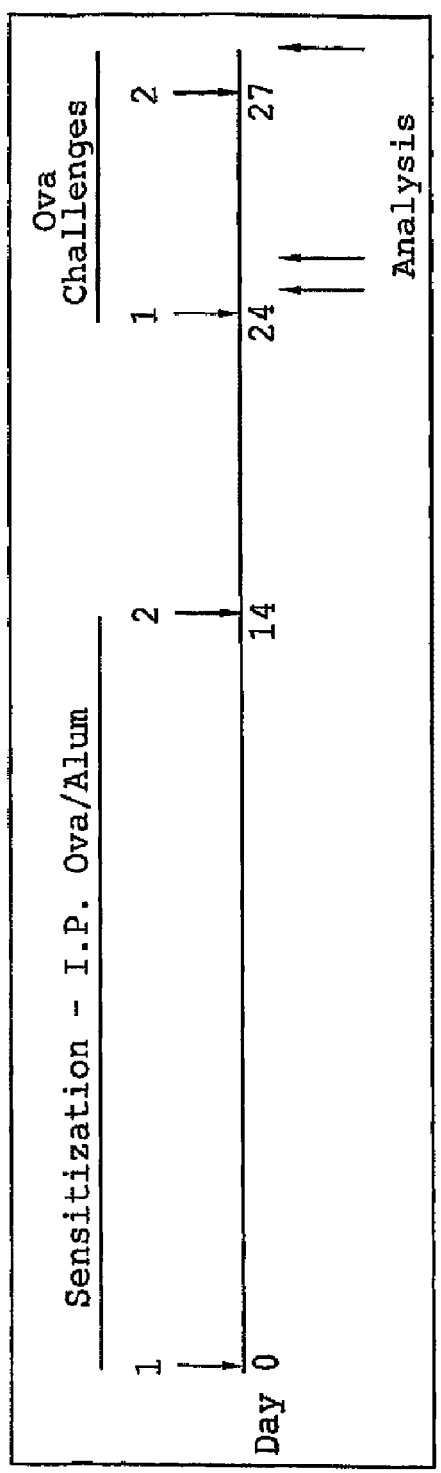
FIG. 2A provides a schematic representation of one embodiment of the allergen challenge protocol. Mice received two intraperitoneal injections with ovalbumin (OVA) (100 μg) and alum (1 mg) on days 0 and 14. Subsequently, mice were challenged with OVA (50 μg) or saline intranasally and analyzed 3 hours or 18 hours after the 1$^{st}$ or 2$^{nd}$ allergen challenge.

In order to reproducibly and accurately identify genes differentially expressed in a well established model of asthma, mice were intraperitoneally sensitized with the allergen ovalbumin (OVA) in the presence of the adjuvant alum on two separate occasions separated by 14 days (FIG. 2A and Example 1). Subsequently, replicate mice were challenged with intranasal OVA or saline (control) on two occasions separated by 3 days. Eighteen hours after the last allergen challenge, one lobe of the murine lung was subjected to histological analysis and the remainder of the lungs was used for RNA analysis. As expected, histological analysis revealed that the allergen challenged mice had marked eosinophil-rich inflammatory response, as previously reported (Rothenberg, M. E., MacLean, J. A., Pearlman, E., Luster, A. D., and Leder, P. 1997. Targeted disruption of the chemokine eotaxin partially reduces antigen-induced tissue eosinophilia. *J Exp Med* 185:785-790).

In order to verify the presence of allergen induced mRNA transcripts, RNA was subjected to Northern blot analysis and analyzed for induction of the chemokine eotaxin-1, which has previously been shown to be significantly induced by allergen challenge (Rothenberg, et al., 1997, supra). The finding that the allergen-challenged lungs had abundant eotaxin-1 mRNA levels, whereas saline treated mice had very low levels, verified the experimental induction protocol.

Next, the RNA was subjected to microarray analysis utilizing the AFFYMETRIX chip U74Av2 that contains oligonucleotide probe sets representing 12,422 genetic elements (Example 2). The microarray data was further analyzed according to the methods provided in Example 4.

Figure 2B:
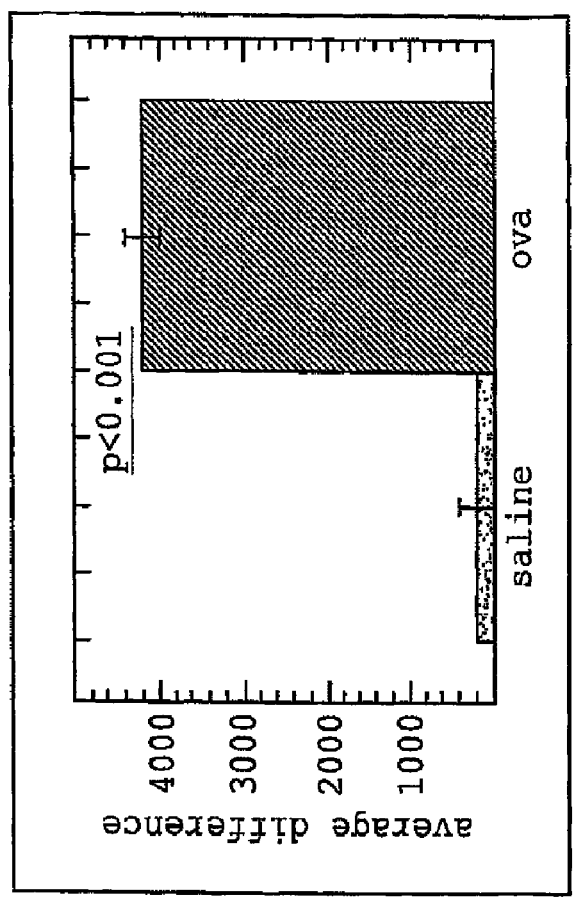
FIG. 2B is a bar graph illustrating a quantitative analysis of the eotaxin-1 signal for saline and ova-treated mice. Error bars represent the standard deviation.

Comparison of the two saline challenged mice to each other and comparison of the two allergen challenged mice to each other revealed $\leq 1\%$ of the genes changing >2-fold. An analysis of present genes in a scatter plot revealed relatively few points outside of the 2-fold boundaries. In contrast, pairwise comparison of allergen challenged mice to saline challenged mice revealed a >2-fold change in 6.5±0.8% of the genes. As indicated, eotaxin-1 was reproducibly identified in the allergen-induced genes (FIG. 2B). Quantitative analysis of average difference signal for eotaxin-1 between allergen and saline revealed a 25-fold induction (P=0.001). Collectively, this data validated the experimental analysis and illustrated the potential value of the scientific approach employed; thus, providing the impetus for the next set of experiments.

Genetic Control of Asthma: Genes Expressed and Overlapping Induced Genes

Figure 3:
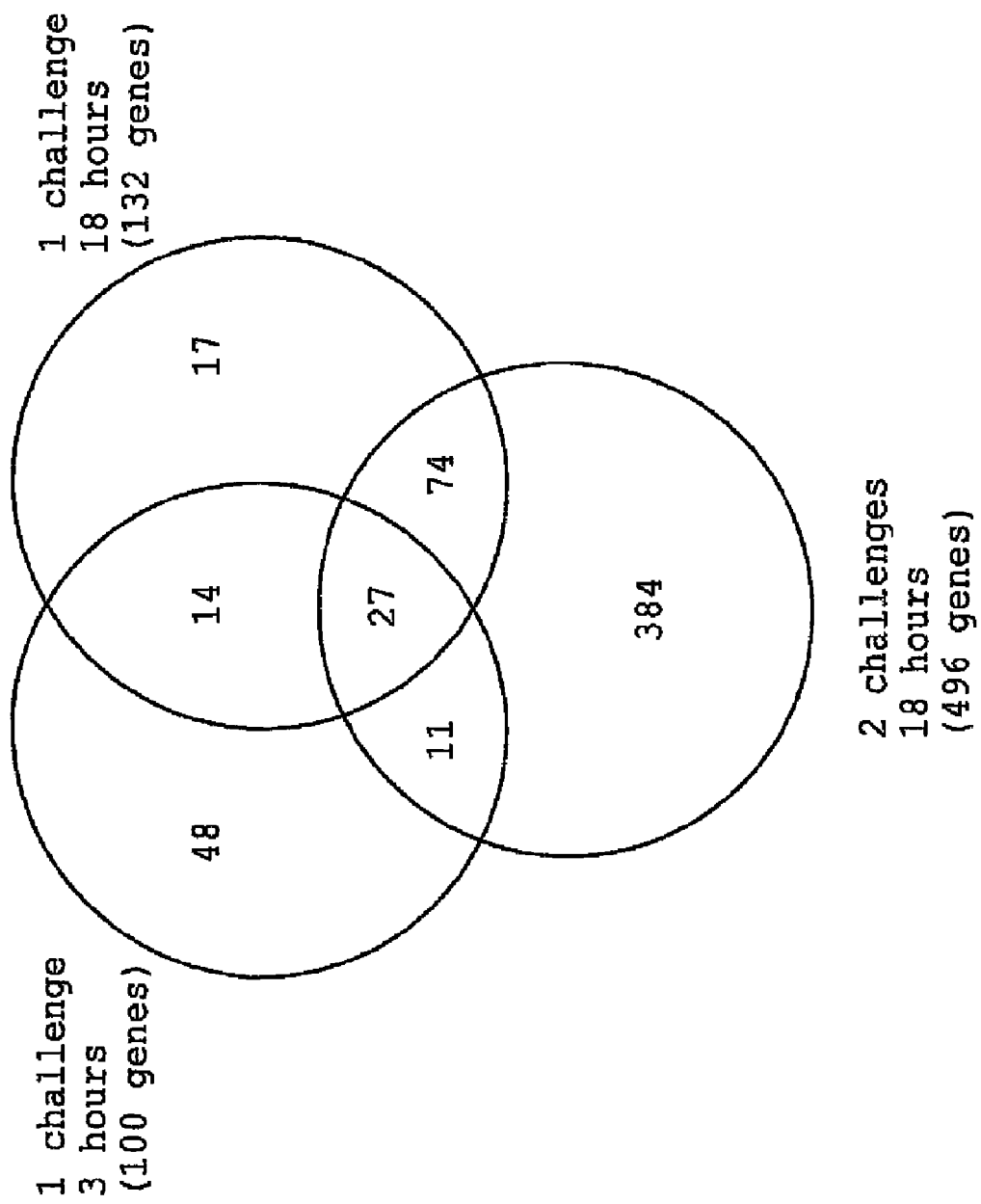
FIG. 3 is a Venn diagram that illustrates the overlap of induced genes at specific phases of experimental asthma in OVA-treated mice.

Additional experiments were performed to define the pattern of lung mRNA transcripts in a larger set of mice during acute and chronic phases of the experimental asthma regime. The hypothesis was that a unique set of genes would be induced acutely after the first allergen challenge compared to a later time point after the second challenge. First, an early time point (3 hours) after the first allergen encounter was analyzed, based on the reasoning that this analysis would provide insight into the initial responses to allergen exposure in the lung. Indeed, only 100 genes were induced by early encounter with allergen (FIG. 3).

Next, the genes induced 18 hours after the first allergen challenge were analyzed. At this later time point, there was a progressive induction of 132 genes, many of which were not evident acutely after allergen challenge. Indeed, 41 of the early activation genes remained elevated; whereas 91 additional genes increased (FIG. 3). Unlike the acute time point, there was not a unique "genetic signature" compared with genes induced 18 hours after two allergen challenges. In fact, most genes that were induced 18 hours after the first allergen challenge, were further increased following the second challenge.

The characterization of genes induced during the relatively "chronic" phase of experimental asthma was undertaken in order to provide important insight into the pathogenesis of chronic allergic lung responses. Indicative of an expansion in the adaptive immune response, during the chronic phase of experimental asthma, immune-related genes predominated in the increased group (44%) compared to the decreased group (4.4%). In contrast, genes involved in development and homeostasis composed the majority of the decreased genes (54%), while only comprising 20% of the increased genes.

Comparison of Allergen Specific Genes: OVA vs. *Asperigillus* Induced Asthma

Figure 4:
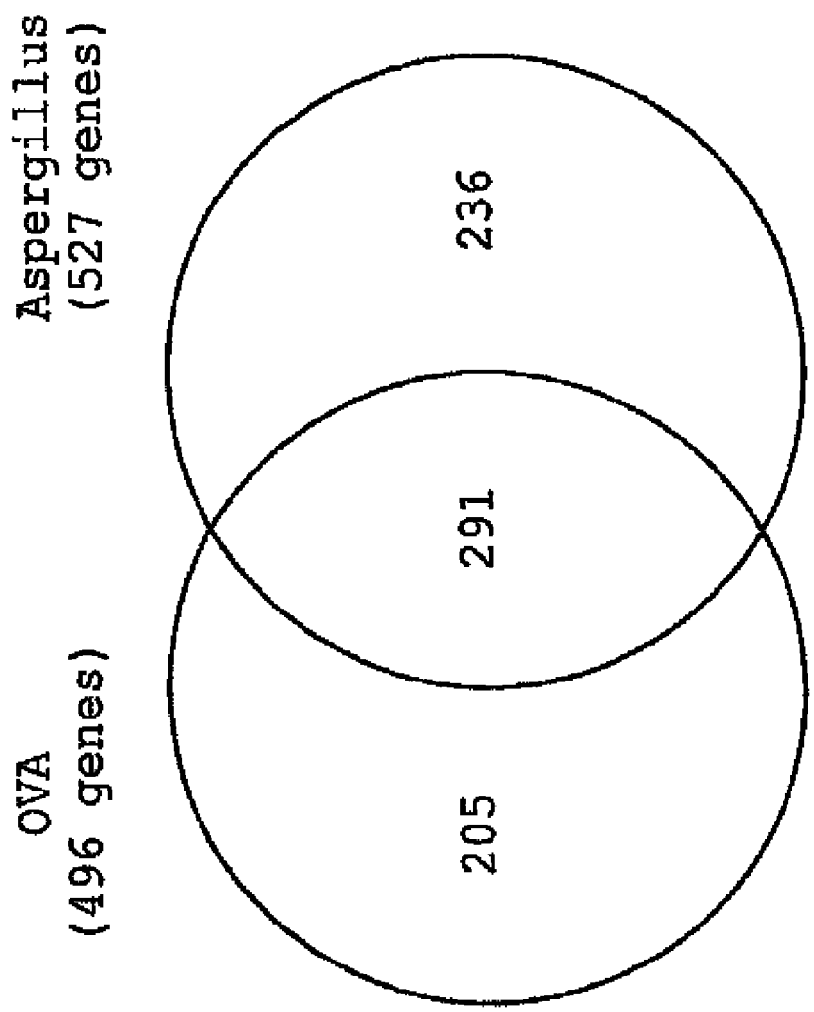
FIG. 4 is a Venn diagram that illustrates the overlap of genes induced by the allergens OVA and *Aspergillis fumigatus* antigen in mice.

The next focus was the comparison of global transcript profiles in two independent models of asthma. Accordingly, experimental asthma induced by *Aspergillus fumigatis* antigens was analyzed because this model involves a unique mucosal sensitization route (intranasal) compared with the OVA model (Huang, W. W., Garcia-Zepeda, E. A., Sauty, A., Oettgen, H. C., Rothenberg, M. E., and Luster, A. D. 1998. Molecular and biological characterization of the murine leukotriene $B_4$ receptor expressed on eosinophils. *J. Exp. Med.* 188:1063-1074). and because *Aspergillus fumigatis* is a ubiquitous and common aeroallergen. Importantly, both asthma models have similar phenotypes including Th2 associated-eosinophilic inflammation, mucus production, and airway hyperresponsiveness. Eighteen hours after nine doses of intranasal *Aspergillus fumigatus* allergen challenge, lung RNA was subjected to the same microarray and data processing analyses as that performed 18 hours after the last OVA challenge. Compared with mice challenged with intranasal saline, *Aspergillus fumigatus* challenged mice had 527 genes induced (FIG. 4).

The majority (63% of OVA and 61% of *Aspergillus*) of the induced transcripts overlapped between the two experimental asthma models, however, 182 (37% of the 496 genes increased following two OVA challenges) and 208 (39% of genes increased by *Aspergillus*) genes were unique for the OVA and *Aspergillus fumigatus* models, respectively.

Comparing the genes induced by both asthma models revealed specific dysregulation of genes upstream of several signaling pathways such as 12-lipoxygenase in the OVA model. Thus, despite roughly similar asthma phenotypes, the two independent asthma models were characterized by a large number of uniquely dysregulated genes. This indicates that individual allergic airway inflammatory states are likely to have largely divergent genetic signatures and operational pathways.

Experimental Asthma is Associated with Induction of Genes Involved in L-arginine Metabolism.

The results identified a set of 291 genes (Table 1) that were commonly involved in disease pathogenesis, rather than unique to a particular allergen or mode of disease induction. These asthma signature genes provide a valuable opportunity to define new pathways involved in the pathogenesis of allergic airway inflammation. As one example, the high level of transcripts for genes involved in metabolism of L-arginine was striking.

TABLE 1

Asthma Signature Genes

| Systematic | OVA-Normalized | Asp-Normalized | Genbank Accession Number | Gene Description |
|---|---|---|---|---|
| 101616_at | 225540 | 39246.668 | M19911 | immunoglobulin kappa chain |
| 93717_at | 108733.336 | 90790 | NM_011331 | SCYA12 (MCP-5) |
| 101436_at | 84566.664 | 32.45614 | NM_008599 | SCYB9 (Mig) |
| 101027_s_at | 98806.664 | 4.946778 | NM_013917 | pituitary tumor-transforming 1 |
| 101803_at | 87700 | 8790 | AJ010792 | Muc5AC-like gene |
| 93755_at | 89523.336 | 101145 | NM_023881 | resistin like beta |
| 94330_at | 72116.664 | 103670 | AK002734 | EST |
| 99578_at | 59720 | 55400 | NM_011623 | topoisomerase (DNA) II alpha |
| 103289_at | 38193.332 | 60.650017 | NM_016869 | low density lipoprotein receptor-related protein 4 |
| 103088_at | 16663.334 | 9.3210535 | NM_007697 | close homolog of L1 |
| 102782_at | 15660 | 8526.667 | BC006884 | EST |
| 162287_r_at | 157.68481 | 95.58796 | NM_017474 | chloride channel calcium activated 3 |
| 94761_at | 101.713 | 50.726936 | X70058 | EST |
| 93097_at | 98.76876 | 108.230156 | NM_007482 | arginase 1 |
| 101870_at | 48.64205 | 224780 | V00793 | immunogloblin heavy chain (IgG1) |
| 92459_at | 43.723305 | 383.66388 | NM_021443 | SCYA8 (MCP-2) |
| 161968_f_at | 35.185265 | 22.420723 | D83648 | CCR5 |
| 93099_f_at | 30.061855 | 57323.332 | NM_011121 | polo-like kinase homolog |
| 92742_at | 24.619387 | 22.648064 | U77462 | SCYA11 (eotaxin-1) |
| 102337_s_at | 23.430752 | 19.95273 | M31312 | beta Fc receptor type II |
| 100127_at | 23.669697 | 11203.333 | BC018397 | cellular retinoic acid binding protein II |
| 102736_at | 23.493471 | 68.94838 | M19681 | CCL2 (JE) |
| 102204_at | 23.287586 | 67830 | L36434 | Kreisler |
| 101075_f_at | 23.076147 | 18.475286 | NM_011783 | anterior gradient 2 |
| 160159_at | 21.610453 | 9.571152 | NM_007629 | cyclin B1, related sequence 1 |
| 101024_i_at | 16.942549 | 240.79553 | AJ005559 | SPRR2A |
| 95338_s_at | 16.297825 | 78.58169 | NM_008605 | matrix metalloproteinase 12 |
| 103024_at | 15.965419 | 274.74274 | NM_007403 | a disintegrin and metalloprotease domain 8 |
| 101752_f_at | 15.405419 | 5.4361067 | BC003888 | immunoglobulin heavy chain |
| 96973_f_at | 15.03831 | 2.604794 | X02468 | immunoglobulin kappa chain |
| 97563_f_at | 15.637967 | 8.38196 | AF042798 | VAV |
| 94383_at | 13.320507 | 10.951402 | NM_009364 | tissue factor pathway inhibitor 2 |
| 96336_at | 13.159998 | 4.711911 | NM_025961 | glycine amidinotransferase |
| 96081_at | 12.9895525 | 3.1729324 | X60980 | EST |

TABLE 1-continued

Asthma Signature Genes

| Systematic | OVA-Normalized | Asp-Normalized | Genbank Accession Number | Gene Description |
|---|---|---|---|---|
| 101747_f_at | 12.68841 | 14.8531 | BC010324 | EST |
| 102719_f_at | 11.682585 | 11.263889 | D83648 | CCR5 |
| 95339_r_at | 11.653785 | 32.66752 | NM_008605 | matrix metalloproteinase 12 |
| 101464_at | 11.270443 | 6.67038 | NM_011593 | tissue inhibitor of metalloproteinase |
| 97574_f_at | 10.615792 | 3.4934838 | AF036736 | Tyk2 |
| 99701_f_at | 10.283908 | 15.477636 | AJ005560 | pheromone receptor V2R1 |
| 99412_at | 10.213736 | 7.2845774 | U29677 | 5HT1B |
| 102718_at | 9.953823 | 5.3958616 | AF022990 | CCR5 |
| 101320_f_at | 11.34985 | 4.766794 | L28059 | Ig B cell antigen receptor gene |
| 101025_f_at | 9.405751 | 12.41217 | AJ005559 | SPRR2A |
| 103507_at | 9.453025 | 3.9533896 | X93328 | EGF-like module containing, mucin-like, hormone receptor-like sequence 1 |
| 104388_at | 9.408694 | 18.71653 | NM_011338 | SCYA9 (MRP-2) |
| 101871_f_at | 9.909628 | 8.040251 | BC003435 | immunoglobulin heavy chain (IgG1) |
| 102860_at | 8.93476 | 5.155658 | BC002065 | serine protease inhibitor 2-1 |
| 97575_f_at | 9.2360935 | 2.769376 | AF036737 | immunoglobulin heavy chain |
| 98372_at | 8.64797 | 13.498421 | AF253409 | aldehyde dehydrogenase family 1, subfamily A3 |
| 93302_at | 8.627996 | 22.25536 | U78770 | trefoil protein; spasmolytic polypeptide (mSP) gene |
| 102155_f_at | 9.713297 | 171.56984 | K03461 | immunoglobulin kappa chain |
| 103362_at | 8.536932 | 8.227436 | NM_008965 | prostaglandin E receptor 4 (subtype EP4) |
| 104374_at | 8.047283 | 5.9670243 | NM_009252 | serine protease inhibitor 2-2 |
| 103715_at | 7.910169 | 10.097453 | NM_009132 | scinderin |
| 97008_f_at | 7.836625 | 3.1931891 | L33943 | sperm motility kinase 2 |
| 92737_at | 7.588307 | 9.6024885 | U20949 | lymphoid-specific interferon regulatory factor (LSIRF) |
| 93858_at | 7.483522 | 2.8942115 | NM_021274 | SCYB10 (IP-10) |
| 100362_f_at | 7.8602414 | 4.154518 | X02463 | immunoglobulin heavy chain |
| 98765_f_at | 8.378079 | 4.30979 | U23095 | Mus musculus CAG trinucleotide repeat mRNA |
| 97567_f_at | 7.817849 | 374396.66 | AF045026 | immunoglobulin kappa chain |
| 96020_at | 7.235781 | 5.5908856 | NM_009777 | complement component 1, q subcomponent, beta polypeptide |
| 93871_at | 7.205034 | 220793.33 | L32838 | interleukin 1 receptor antagonist |
| 99457_at | 7.0135965 | 11.358481 | X82786 | antigen identified by monoclonal antibody Ki 67 |
| 92898_at | 6.921668 | 10.98594 | NM_007825 | cytochrome P450, 7b1 |
| 99413_at | 6.865213 | 6.676117 | NM_009912 | CCR1 |
| 93441_at | 6.86 | 8.001611 | BC002320 | EST |
| 161898_i_at | 6.715635 | 4.932269 | NM_013604 | metaxin |
| 99384_at | 6.4949207 | 3.227118 | M13945 | 2'-5' oligoadenylate synthetase |
| 100299_f_at | 7.053511 | 6.5434785 | U68543 | immunoglobulin kappa chain |
| 100360_f_at | 6.9094634 | 3.2684014 | X02466 | immunoglobulin heavy chain |
| 103821_at | 6.4850364 | 3.5823884 | NM_011799 | cell division cycle 6 homolog |
| 104712_at | 6.410893 | 6.9562626 | L00039 | c-myc |
| 94792_at | 6.60177 | 5.1981874 | AV230061 | EST |
| 97577_f_at | 7.0308433 | 7.3983607 | AF042086 | immunoglobulin heavy chain |
| 95749_at | 6.5904636 | 4.886688 | AK014338 | arginine-rich, mutated in early stage tumors |
| 100376_f_at | 7.1667223 | 3.663984 | AF025445 | immunoglobulin heavy chain |
| 99564_at | 6.2264986 | 5.7295732 | NM_010931 | nuclear protein 95 |
| 96972_f_at | 6.6524925 | 10.578374 | X00651 | immunoglobulin kappa chain |
| 97826_at | 6.095861 | 4.748955 | BF578028 | EST |
| 101920_at | 6.945455 | 10730 | AF036898 | DNA polymerase epsilon, subunit 2 |
| 102076_at | 6.6639376 | 9.057281 | AJ235940 | immunoglobulin kappa gene |
| 92694_at | 5.997402 | 2.850934 | NM_009892 | chitinase 3-like 3 |
| 98500_at | 5.9301085 | 4.8730392 | D13695 | interleukin 1 receptor-like 1 |
| 160509_at | 5.902416 | 3.263418 | NM_023186 | chitinase, acidic |
| 101716_at | 6.3816996 | 9.589625 | AF017260 | ribonuclease 5 precursor |
| 94425_at | 5.785283 | 2.5883076 | NM_010745 | lymphocyte antigen 86 |
| 100721_f_at | 6.602228 | 4.1458287 | NM_019633 | immunoglobulin heavy chain |
| 161000_i_at | 5.7863874 | 5.6846313 | BC009096 | EST |
| 97576_f_at | 5.836974 | 6.7057757 | AF036738 | immunoglobulin heavy chain |
| 103492_at | 5.7621274 | 34.26642 | NM_019696 | metallocarboxypeptidase CPX-1 |
| 92471_i_at | 5.6972423 | 4.1381645 | NM_011408 | schlafen 2 |
| 102157_f_at | 6.223431 | 8.301306 | M15520 | immunoglobulin kappa chain |
| 104423_at | 5.5257926 | 4.04915 | AK012919 | EST |
| 97566_f_at | 5.7326064 | 3.3756723 | AF045024 | cell cycle regulatory transcription factor DP1 |
| 99850_at | 5.6840267 | 13.790022 | X01857 | EST |
| 99799_at | 5.2402177 | 4.7810144 | NM_011691 | vav oncogene |
| 103977_at | 5.242547 | 5.874125 | NM_007972 | coagulation factor X |
| 100682_f_at | 5.7159605 | 6.4657617 | BC018315 | immunoglobulin heavy chain (IgM) |

TABLE 1-continued

Asthma Signature Genes

| Systematic | OVA-Normalized | Asp-Normalized | Genbank Accession Number | Gene Description |
| --- | --- | --- | --- | --- |
| 102712_at | 5.00839 | 114.47321 | X03505 | serum amyloid A (SAA) 3 |
| 95546_g_at | 5.007943 | 5.40468 | NM_010512 | insulin-like growth factor 1 |
| 102334_at | 4.9804444 | 5.37676 | NM_010071 | downstream of tyrosine kinase 2 |
| 161476_at | 4.8584557 | 6.1884484 | NM_011179 | prosaposin |
| 94747_at | 5 | 11.483464 | NM_007780 | colony stimulating factor 2 receptor, beta 1, low-affinity (granulocyte-macrophage) |
| 160973_at | 4.754941 | 5.9356265 | AV113368 | EST |
| 94774_at | 4.751594 | 3.7062113 | NM_008327 | interferon activated gene 202A |
| 97519_at | 4.717509 | 2.4604154 | NM_009263 | secreted phosphoprotein 1 |
| 92406_at | 4.697705 | 3.7283828 | D31956 | CD7 antigen |
| 97527_at | 4.71631 | 6.0879946 | NM_025415 | EST |
| 104509_at | 4.7671666 | 3.9175062 | NM_009890 | cholesterol 25-hydroxylase |
| 92736_at | 4.6499114 | 2.43423 | NM_007514 | solute carrier family 7 (cationic amino acid transporter, y+ system), member 2 |
| 94357_at | 4.6305223 | 15.957945 | NM_019810 | solute carrier family 5, member 1 |
| 103563_at | 4.566576 | 3.228621 | AK015966 | EST |
| 100325_at | 4.565603 | 5.2161465 | NM_008147 | glycoprotein 49 A |
| 101718_f_at | 4.6051664 | 2.784962 | U68543 | immunoglobulin kappa chain |
| 92223_at | 4.38655 | 3.4771063 | NM_007574 | complement component 1, q subcomponent, c polypeptide |
| 92877_at | 4.3477926 | 3.3488877 | NM_009369 | transforming growth factor, beta induced, 68 kDa |
| 162362_f_at | 4.7214866 | 13.813264 | NM_011607 | tenascin C |
| 92217_s_at | 4.1649747 | 6.179337 | U05265 | BALB/c gp49B |
| 104174_at | 4.2072635 | 10.121372 | NM_008813 | ectonucleotide pyrophosphatase/phosphodiesterase 1 |
| 99057_at | 4.254866 | 2.0512702 | M12379 | EST |
| 161173_f_at | 4.3232756 | 2.716511 | AV229143 | EST |
| 103226_at | 4.126826 | 3.1783247 | NM_008625 | mannose receptor, C type 1 |
| 95753_at | 4.1263847 | 2.7586782 | BG175174 | EST |
| 97763_at | 4.260391 | 4.074452 | L11455 | neutrophil cytosolic factor 1 |
| 99541_at | 4.104807 | 24.215685 | AJ223293 | kinesin-like 1 |
| 96971_f_at | 4.3104587 | 3.9387467 | X00652 | immunoglobulin heavy chain |
| 104308_at | 4.0227704 | 3.8388264 | NM_021334 | integrin alpha X |
| 92639_at | 4.0441484 | 7.0198045 | BC014711 | serine/threonine kinase 6 |
| 102585_f_at | 4.230241 | 2.8028138 | AB017349 | immunoglobulin light chain |
| 96964_at | 3.894107 | 17.932245 | L14554 | immunoglobulin light chain |
| 102354_at | 3.9053602 | 4.594614 | BC004617 | EST |
| 101640_f_at | 4.131984 | 4.4899344 | U68543 | immunoglobulin kappa chain |
| 101331_f_at | 4.1094975 | 10.231754 | U68543 | immunoglobulin kappa chain |
| 92762_at | 3.7854714 | 18.729609 | NM_011999 | C-type (calcium dependent, carbohydrate recognition domain) lectin, superfamily member 6 |
| 99979_at | 3.879566 | 4.449123 | NM_009994 | cytochrome P450, 1b1, benz[a]anthracene inducible |
| 102755_at | 3.8250763 | 42.851036 | NM_010584 | intelectin |
| 99876_at | 3.7478104 | 2.71695 | AJ131777 | src-like adaptor protein |
| 100771_at | 3.7049873 | 52.361767 | Y17159 | lymphocyte antigen 57 |
| 102025_at | 3.746413 | 11.825412 | NM_018866 | SCYB13 (BLC/BCA-1) |
| 101521_at | 3.7192738 | 3.4149444 | BC004702 | baculoviral IAP repeat-containing 5 |
| 98562_at | 3.5959404 | 3.0973809 | NM_007572 | complement component 1, q subcomponent, alpha polypeptide |
| 100116_at | 3.8081882 | 2.2723222 | NM_026515 | EST |
| 103210_at | 3.5521066 | 3.5796819 | NM_007781 | colony stimulating factor 2 receptor, beta 2, low-affinity (granulocyte-macrophage) |
| 97444_at | 3.5403333 | 3.7394972 | NM_023065 | interferon gamma inducible protein 30 |
| 103040_at | 3.5184398 | 5.563819 | NM_009856 | CD83 antigen |
| 92832_at | 3.5796704 | 2.58255 | NM_009896 | cytokine inducible SH2-containing protein 1 |
| 101468_at | 3.499593 | 2.9337993 | X12905 | properdin factor, complement |
| 101656_f_at | 3.572765 | 5.152894 | U68543 | immunoglobulin kappa chain |
| 160406_at | 3.5679104 | 6.6120887 | AJ006033 | ctsk |
| 161511_f_at | 3.6552558 | 2.4223258 | AK019325 | EST |
| 100479_at | 3.5037563 | 5.1488533 | NM_007872 | DNA methyl transferase 3A |
| 96784_at | 3.5443184 | 7.2892175 | BE573736 | EST |
| 98473_at | 3.414378 | 4.315487 | NM_009705 | arginase II |
| 103690_at | 3.4046066 | 2.7740142 | AW125574 | EST |
| 97411_at | 3.432237 | 5.097896 | NM_007900 | ect2 oncogene |
| 102990_at | 3.3784416 | 3.176364 | AK019448 | procollagen, type III, alpha 1 |
| 101913_at | 3.3619032 | 2.298871 | NM_010423 | hairy/enhancer-of-split related with YRPW motif 1 |
| 96511_s_at | 3.349278 | 2.489442 | NM_011691 | vav oncogene |
| 96515_at | 3.3318715 | 5.013796 | U70430 | estrogen receptor beta |
| 99509_s_at | 3.304514 | 2.4309058 | NM_010589 | Janus kinase 3 |

TABLE 1-continued

Asthma Signature Genes

| Systematic | OVA-Normalized | Asp-Normalized | Genbank Accession Number | Gene Description |
|---|---|---|---|---|
| 102658_at | 3.29768 | 2.4413974 | NM_010555 | interleukin 1 receptor, type II |
| 99405_at | 3.4179718 | 2.6559134 | Z95479 | immunoglobulin kappa chain |
| 102001_at | 3.2696967 | 4.6717634 | NM_009104 | ribonucleotide reductase M2 |
| 100772_g_at | 3.2473373 | 3.9850318 | Y17159 | lymphocyte antigen 57 |
| 100156_at | 3.2375228 | 5.1784253 | NM_008566 | mini chromosome maintenance deficient 5 |
| 102884_at | 3.2394269 | 5.047297 | NM_010566 | inositol polyphosphate-5-phosphatase, 145 kDa |
| 98772_at | 3.2060094 | 9.574579 | NM_009141 | SCYB5 (LIX) |
| 98859_at | 3.1933463 | 3.7756183 | M99054 | glucose dependent insulinotropic polypeptide |
| 93465_at | 3.1908364 | 2.0911632 | AK020278 | EST |
| 102697_at | 3.2435853 | 50750 | NM_019640 | phosphotidylinositol transfer protein, beta |
| 104548_at | 3.1858604 | 2.3911338 | NM_009434 | tumor-suppressing subchromosomal transferable fragment 3 |
| 160446_at | 3.0992258 | 2.0170536 | U46068 | von Ebner minor salivary gland protein mRNA |
| 92918_at | 3.2433689 | 3.870666 | U66079 | coagulation factor VII |
| 99926_at | 3.0930579 | 2.6117299 | AB001489 | EST |
| 98034_at | 3.0988965 | 2.399438 | NM_010387 | histocompatibility 2, class II, locus Mb1 |
| 103441_at | 3.1662524 | 2.6342456 | NM_007788 | casein kinase II, alpha 1 related sequence 4 |
| 101868_i_at | 3.0873947 | 3.2774441 | NM_010388 | histocompatibility 2, class II, locus Mb2 |
| 104065_at | 3.104958 | 2.903548 | AB042828 | EDEM, similar to alpha-mannosidase |
| 103418_at | 3.0449538 | 4.5369325 | BC003335 | EST |
| 103201_at | 3.1155026 | 2.5040376 | NM_009445 | Ttk protein kinase |
| 102892_at | 2.965567 | 2.3691757 | U31908 | potassium voltage-gated channel, shaker-related subfamily, beta member 2 |
| 101020_at | 3.0216243 | 4.072408 | NM_009982 | cathepsin C |
| 102372_at | 2.962975 | 4.9571853 | BC006026 | immunoglobulin joining chain |
| 96295_at | 2.980223 | 4.0674667 | BC004827 | DNA segment, Chr 8, ERATO Doi 814, expressed |
| 103089_at | 2.977104 | 2.9797423 | X53526 | CD48 antigen |
| 160663_at | 3.0093396 | 3.73139 | BC011308 | EST |
| 160119_at | 2.9357014 | 2.8572135 | NM_007961 | TEL oncogene |
| 104547_at | 3.0306945 | 2.5664012 | J00388 | dihydrofolate reductase gene |
| 162198_f_at | 2.930065 | 3.8110802 | NM_009139 | SCYA6 (C10, MRP-1) |
| 98948_at | 2.913645 | 2.3195322 | BE914613 | EST |
| 92472_f_at | 2.915114 | 2.61941 | NM_011408 | schlafen 2 |
| 92232_at | 2.943417 | 3.4743614 | NM_007707 | cytokine inducible SH2-containing protein 3 |
| 101878_at | 2.8530445 | 4.578556 | NM_007654 | CD72 antigen |
| 94294_at | 2.7738435 | 2.6131907 | NM_007630 | cyclin B2 |
| AFFX-TransRecMur/X57349_M_at | 2.8628469 | 39776.668 | NM_011638 | transferrin receptor |
| 102809_s_at | 2.7613506 | 2.1943572 | BC011474 | lymphocyte protein tyrosine kinase |
| 99973_s_at | 2.749837 | 5.1267667 | NM_019664 | potassium inwardly-rectifying channel, subfamily J, member 15 |
| 103205_at | 2.698056 | 3.892967 | NM_016921 | T-cell, immune regulator 1 |
| 97421_at | 2.7415438 | 2.267686 | NM_008017 | fibroblast growth factor inducible 16 |
| 95148_at | 2.6961179 | 2.801927 | NM_016895 | adenylate kinase 2 |
| 95032_at | 2.7158015 | 6.0467033 | BC005475 | DNA segment, Chr 7, ERATO Doi 348, expressed |
| 95532_at | 2.7031207 | 2.6633081 | BG070246 | EST |
| 98035_g_at | 2.6737032 | 2.1324506 | NM_010387 | histocompatibility 2, class II, locus Mb1 |
| 161103_at | 2.6972256 | 7.9766407 | BG064768 | EST |
| 103662_at | 2.6623814 | 2.36007 | NM_008677 | neutrophil cytosolic factor 4 |
| 104464_s_at | 2.6995149 | 2.8936243 | BC011472 | EST |
| 160298_at | 2.701887 | 2.6409597 | AK011256 | EST |
| 162206_f_at | 2.6395187 | 2.7735467 | NM_007707 | cytokine inducible SH2-containing protein 3 |
| 102310_at | 2.622947 | 2.9848456 | NM_009137 | SCYA22 (ABCD-1) |
| 98433_at | 2.5899887 | 2.410541 | BC002031 | BH3 interacting domain death agonist |
| 99974_at | 2.6164083 | 6.7606096 | NM_019664 | potassium inwardly-rectifying channel, subfamily J, member 15 |
| 104099_at | 2.6075976 | 2.9022658 | NM_009402 | peptidoglycan recognition protein |
| 104147_at | 2.568291 | 2.4725318 | NM_053179 | sialic acid synthase |
| 101506_at | 2.5859814 | 2.4086373 | NM_021336 | U2 small nuclear ribonucleoprotein polypeptide A' |
| 103203_f_at | 2.611314 | 4.093791 | W29450 | EST |
| 93112_at | 2.5585814 | 3.6827056 | NM_008564 | mini chromosome maintenance deficient 2 |
| 104097_at | 2.586194 | 4.50625 | U89795 | budding uninhibited by benzimidazoles 1 homolog |
| 99669_at | 2.5426898 | 2.2998266 | NM_008495 | lectin, galactose binding, soluble 1 |
| 99149_at | 2.6465125 | 4.2806926 | NM_025863 | EST |
| 102326_at | 2.535973 | 4.4882274 | NM_010877 | neutrophil cytosolic factor 2 |
| 102293_at | 2.5311453 | 2.1284976 | NM_009578 | zinc finger protein, subfamily 1A, 1 (Ikaros) |

TABLE 1-continued

Asthma Signature Genes

| Systematic | OVA-Normalized | Asp-Normalized | Genbank Accession Number | Gene Description |
|---|---|---|---|---|
| 92833_at | 2.515559 | 5.7817793 | NM_010401 | histidine ammonia lyase |
| 92540_f_at | 2.5182536 | 2.2194166 | Z67748 | spermidine synthase gene |
| 92633_at | 2.4970362 | 4.8684945 | NM_022325 | cathepsin Z |
| 94521_at | 2.5898051 | 2.126383 | NM_009878 | cyclin-dependent kinase inhibitor 2D (p19, inhibits CDK4) |
| 102748_at | 2.5555553 | 3.159657 | NM_007976 | coagulation factor V |
| 98026_g_at | 2.4942427 | 2.6773672 | NM_010161 | ecotropic viral integration site 2 |
| 104155_f_at | 2.4959242 | 3.0125077 | U19118 | activating transcription factor 3 |
| 104606_at | 2.476346 | 2.9692168 | NM_013706 | CD52 antigen |
| 95423_at | 2.4727428 | 2.26199 | NM_009787 | calcium binding protein, intestinal |
| 102914_s_at | 2.4644232 | 2.763536 | U23778 | hematopoietic-specific early-response A1-b |
| 100322_at | 2.506151 | 3.7979157 | U68543 | immunoglobulin kappa chain |
| 101561_at | 2.5639465 | 3.3606117 | K02236 | metallothionien II |
| 94208_at | 2.4507363 | 2.1223657 | AK005989 | EST |
| 92978_s_at | 2.5112484 | 57173.336 | NM_011111 | serine (or cysteine) proteinase inhibitor, clade B (ovalbumin), member 2 |
| 98968_at | 2.4667523 | 3.6377416 | NM_010864 | myosin Va |
| 93869_s_at | 2.409471 | 2.9823458 | U23781 | hematopoietic-specific early-response A1-d |
| 100955_at | 2.4169822 | 2.8062625 | NM_026024 | EST |
| 94939_at | 2.3913658 | 2.5653691 | NM_007651 | CD53 antigen |
| 94831_at | 2.3831258 | 2.396902 | M65270 | EST |
| 98147_at | 2.3919983 | 2.7486196 | AC002397 | EST |
| 97468_at | 2.373815 | 2.054054 | NM_016904 | CDC28 protein kinase 1 |
| 99333_at | 2.3824167 | 2.1954718 | M80778 | Opioid receptor, delta 1 |
| 97327_at | 2.3735232 | 2.2973487 | NM_007999 | flap structure specific endonuclease 1 |
| 102851_s_at | 2.338283 | 2.0963266 | NM_013545 | hemopoietic cell phosphatase |
| 95608_at | 2.387856 | 3.330935 | NM_007798 | cathepsin B |
| 98025_at | 2.3166697 | 2.6697729 | NM_010161 | ecotropic viral integration site 2 |
| 99051_at | 2.3099425 | 3.3240612 | M36579 | M-caveolin |
| 98822_at | 2.3430436 | 3.46114 | NM_015783 | interferon-stimulated protein (15 kDa) |
| 103016_s_at | 2.2778614 | 3.1853485 | NM_009853 | CD68 antigen |
| 102156_f_at | 2.2706146 | 3.39309 | M80423 | immunoglobulin kappa chain |
| 104701_at | 2.257285 | 3.2854443 | NM_011498 | basic helix-loop-helix domain containing, class B2 |
| 100981_at | 2.2767577 | 4.706134 | NM_008331 | interferon-induced protein with tetratricopeptide repeats 1 |
| 98603_s_at | 2.2418516 | 2.015457 | U20857 | RNA1 homolog (Fug1) |
| 92913_at | 2.2495005 | 2.0332723 | NM_011994 | ATP-binding cassette, sub-family D (ALD), member 2 |
| 102957_at | 2.2281997 | 2.137948 | BC006948 | lymphocyte cytosolic protein 2 |
| 101221_at | 2.219952 | 2.729755 | BG065737 | EST |
| 160314_at | 2.2163954 | 2.1361492 | NM_026438 | EST |
| 96963_s_at | 2.2737944 | 3.4263778 | L14553 | TAX responsive element binding protein 107 |
| 98572_at | 2.2201126 | 2.0962021 | NM_026400 | DnaJ (Hsp40) homolog, subfamily B, member 11 |
| 95348_at | 2.2361295 | 7.687291 | NM_008176 | CXCL1 (GRO-1) |
| 103562_f_at | 2.1999772 | 2.665438 | M26005 | truncated; Mouse endogenous retrovirus truncated gag protein, complete cds, clone del env-1 3.1. |
| 96319_at | 2.1911578 | 3.0398011 | NM_023223 | cell division cycle 20 homolog |
| 96602_g_at | 2.1935015 | 2.0309908 | NM_023268 | quiescin Q6 |
| 102353_at | 2.1822197 | 3.2570171 | NM_008404 | integrin beta 2 |
| 94367_at | 2.1611505 | 2.059546 | NM_030724 | uridine-cytidine kinase 2 |
| 97894_at | 2.162856 | 2.2836409 | AF109905 | TLP21 (21-kDa TBP-like protein) |
| 98996_at | 2.160693 | 2.2494855 | L29479 | serine/threonine kinase 18 |
| 99632_at | 2.1773741 | 3.8635976 | NM_019499 | MAD2 (mitotic arrest deficient, homolog)-like 1 |
| 104527_at | 2.15728 | 2.0993714 | NM_011234 | RAD51 homolog |
| 95706_at | 2.133574 | 4.0946174 | BI414633 | lectin, galactose binding, soluble 3 |
| 160496_s_at | 2.125215 | 2.1330795 | X62154 | mini chromosome maintenance deficient |
| 97733_at | 2.1464872 | 2.5439253 | NM_007413 | adenosine A2b receptor |
| 98436_s_at | 2.1127503 | 2.2659311 | U54803 | adenylosuccinate synthetase |
| 96357_at | 2.110278 | 2.6390922 | NM_023142 | actin related protein 2/3 complex, subunit 1B (41 kDa) |
| 92567_at | 2.099979 | 2.7503965 | NM_007737 | procollagen, type V, alpha 2 |
| 93861_f_at | 2.1034112 | 2.1940186 | M17327 | Mouse endogenous murine leukemia virus modified polytropic provirus DNA |
| 95803_at | 2.103923 | 2.652425 | D87968 | protein tyrosine phosphatase, non-receptor type substrate 1 |
| 93250_r_at | 2.124497 | 2.4762044 | NM_008252 | high mobility group box 2 |
| 100328_s_at | 2.1381612 | 2.3473186 | NM_011090 | paired-Ig-like receptor A3 |
| 160246_at | 2.099816 | 2.0582118 | BC009090 | EST |

TABLE 1-continued

Asthma Signature Genes

| Systematic | OVA-Normalized | Asp-Normalized | Genbank Accession Number | Gene Description |
|---|---|---|---|---|
| 103614_at | 2.104216 | 2.412715 | NM_019408 | nuclear factor of kappa light polypeptide gene enhancer in B-cells 2, p49/p100 |
| 161984_f_at | 2.093358 | 2.7761269 | AK019448 | procollagen, type III, alpha 1 |
| 93167_f_at | 2.0522046 | 3.1834278 | AF303744 | oxidized LDL receptor (Lox-1) |
| 95159_at | 2.0587687 | 2.1079147 | AK010250 | Mrps18b |
| 97824_at | 2.0229275 | 2.1522021 | NM_026631 | EST |
| 103625_at | 2.0461566 | 2.641253 | NM_054070 | AFG3(ATPase family gene 3)-like 1 |
| 161345_f_at | 2.0326214 | 2.405795 | NM_007825 | cytochrome P450, 7b1 |
| 93495_at | 2.0277393 | 2.0939586 | NM_016764 | peroxiredoxin 4 |
| 93860_i_at | 2.0132427 | 2.0345182 | M17327 | Mouse endogenous murine leukemia virus modified polytropic provirus DNA |

As indicated in Table 1, arginase I (Genbank Accession NM_007482), arginase II (Genbank Accession NM_009705), and the L-arginine transporter cationic amino acid transporter CAT2 (Genbank Accession NM_007514) were strongly induced. Other enzymes involved in L-arginine metabolism, such as argininosuccinate synthetase, L-ornithine decarboxylase and L-ornithine aminotransferase were not significantly different between saline and allergen-challenged mice. Interestingly, microarray analysis revealed very specific dysregulation of arginase compared with nitric oxide synthase (NOS). For example, the hybridization signals for endothelial NOS and neuronal NOS were below background in the saline and allergen-challenged lung (data not shown). While the inducible NOS (iNOS) mRNA was detectable under most conditions, it did not change significantly between saline and allergen challenge.

Northern blot analysis (Example 3) next determined that there was a time and dose-dependent induction of arginase I during the progression of OVA-induced experimental asthma; arginase I was induced 18 hours after the first allergen challenge and even higher following two allergen challenges. Additionally, while arginase II mRNA induction was weaker than arginase I, it was induced earlier in the evolution of experimental asthma. For example, arginase II was readily detectable 3 hours after the first allergen challenge. Furthermore, Northern blot analysis demonstrated that CAT2 was induced by allergen challenge, with expression already notable 3 hours after the first allergen challenge. The iNOS mRNA was weakly detectable and was not significantly induced by OVA challenge. Additionally, compared with mice challenged with nine doses of intranasal saline, *Aspergillus fumigatus*-challenged mice had marked expression of arginase I, arginase II, and CAT2. Consistent with the results in the OVA model, there were only low levels of induction of iNOS mRNA. Thus, the induction of arginase and CAT2 by allergen challenge was not specific to the antigen employed but appeared to be part of the genetic program of experimental asthma.

In addition, Table 2 illustrates genes that were found to be strongly up-regulated in a model of gastrointestinal allergies by the methods described in Example 14.

TABLE 2

Allergy Signature Genes

| Systematic | Common | Genbank | Description |
|---|---|---|---|
| 94330_at | Npl | NM_028749 | N-acetylneuraminate pyruvate lyase |
| 99578_at | Top2a | NM_011623 | topoisomerase (DNA) II alpha |
| 102782_at | 5430416A05Rik | NM_024242 | RIKEN cDNA 5430416A05 gene |
| 94761_at | Ccl7 | X70058 | chemokine (C—C motif) ligand 7 |
| 161968_f_at | Cmkbr5 | D83648 | chemokine (C—C) receptor 5 |
| 92742_at | Ccl11 | U77462 | small chemokine (C—C motif) ligand 11 |
| 102736_at | Ccl2 | M19681 | chemokine (C—C motif) ligand 2 |
| 102204_at | Mafb | BC038256 | v-maf musculoaponeurotic fibrosarcoma oncogene family, protein B (avian) |
| 101024_i_at | Sprr2a | AJ005559 | small proline-rich protein 2A |
| 99701_f_at | Sprr2b | AJ005560 | small proline-rich protein 2B |
| 101025_f_at | Sprr2a | AJ005559 | small proline-rich protein 2A |
| 102860_at | Serpina3g | BC002065 | serine (or cysteine) proteinase inhibitor, clade A, member 3G |
| 103362_at | Ptger4 | NM_008965 | prostaglandin E receptor 4 (subtype EP4) |
| 103715_at | Scin | NM_009132 | scinderin |
| 92251_f_at | Ifi204 | NM_008329 | interferon activated gene 204 |
| 92780_f_at | env | M90535 | |
| 93871_at | Il1rn | L32838 | interleukin 1 receptor antagonist |
| 102877_at | Gzmb | NM_013542 | granzyme B |
| 98500_at | Il1rl1 | D13695 | interleukin 1 receptor-like 1 |
| 102712_at | Saa3 | X03505 | serum amyloid A 3 |
| 94774_at | Ifi202a | NM_008327 | interferon activated gene 202A |
| 100325_at | Gp49a | NM_008147 | glycoprotein 49 A |

TABLE 2-continued

Allergy Signature Genes

| Systematic | Common | Genbank | Description |
|---|---|---|---|
| 92286_g_at | Il4 | NM_021283 | interleukin 4 |
| 92217_s_at | Gp49b | U05265 | glycoprotein 49 B |
| 103226_at | Mrc1 | NM_008625 | mannose receptor, C type 1 |
| 93776_at | 1500001L15Rik | BC023770 | RIKEN cDNA 1500001L15 gene |
| 103210_at | Csf2rb2 | NM_007781 | colony stimulating factor 2 receptor, beta 2, low-affinity (granulocyte-macrophage) |
| 92832_at | Cish1 | NM_009896 | cytokine inducible SH2-containing protein 1 |
| 99958_at | Mcpt2 | NM_008571 | mast cell protease 2 |
| 94375_at | Hk2 | Y11666 | hexokinase 2 |
| 98772_at | Cxcl5 | NM_009141 | chemokine (C—X—C motif) ligand 5 |
| 98034_at | H2-DMb1 | NM_010387 | histocompatibility 2, class II, locus Mb1 |
| 104696_at | Ctse | AJ009840 | cathepsin E |
| 98948_at | MGC46970 | NM_153547 | hypothetical protein MGC46970 |
| 93411_at | | BG974696 | ESTs |
| 92232_at | Cish3 | NM_007707 | cytokine inducible SH2-containing protein 3 |
| 95673_s_at | Basp1 | AK011545 | brain abundant, membrane attached signal protein 1 |
| 104333_at | G7e-pending | U69488 | G7e protein |
| 161103_at | | BG064768 | ESTs |
| 100062_at | Mcmd | BC031700 | mini chromosome maintenance deficient (*S. cerevisiae*) |
| 162206_f_at | Cish3 | NM_007707 | cytokine inducible SH2-containing protein 3 |
| 98433_at | Bid | BC002031 | BH3 interacting domain death agonist |
| 160469_at | Thbs1 | M62470 | thrombospondin 1 |
| 98045_s_at | Dab2 | NM_023118 | disabled homolog 2 (*Drosophila*) |
| 104155_f_at | Atf3 | BC019946 | activating transcription factor 3 |
| 101561_at | Mt2 | K02236 | metallothionein 2 |
| 98524_f_at | Enc1 | AK008780 | ectodermal-neural cortex 1 |
| 93869_s_at | Bcl2a1d | U23781 | B-cell leukemia/lymphoma 2 related protein A1d |
| 94939_at | Cd53 | NM_007651 | CD53 antigen |
| 104225_at | D2Ertd52e | NM_024225 | DNA segment, Chr 2, ERATO Doi 52, expressed |
| 97327_at | Fen1 | NM_007999 | flap structure specific endonuclease 1 |
| 104701_at | Bhlhb2 | NM_011498 | basic helix-loop-helix domain containing, class B2 |
| 101958_f_at | Tfdp1 | NM_009361 | transcription factor Dp 1 |
| 102957_at | Lcp2 | BC006948 | lymphocyte cytosolic protein 2 |
| 100046_at | Mthfd2 | NM_008638 | methylenetetrahydrofolate dehydrogenase (NAD+ dependent), methenyltetrahydrofolate cyclohydrolase |
| 96602_g_at | Qscn6 | NM_023268 | quiescin Q6 |
| 92567_at | Col5a2 | NM_007737 | procollagen, type V, alpha 2 |
| 160246_at | AA987150 | NM_134131 | expressed sequence AA987150 |
| 102407_at | Mcpt5 | M73760 | mast cell protease 5 |

Arginase Increases in Asthma

It was also discovered that, following induction of experimental asthma, there was a marked increase in lung arginase activity. Consistent with the absence of arginase mRNA in the lung of control mice, the level of arginase activity in the saline-challenged lung was close to background. As a control, arginase activity in the liver was 1522±183 nmol/min/mg protein and 1390±78 nmol/min/mg protein for saline and OVA-challenged mice, respectively.

Thus, it appears that arginine is metabolized by arginase, at least in part, in the asthmatic mouse lung. Furthermore, the variable levels of NO seen in asthma may be an indirect manifestation of arginase activity, an enzyme that functionally inhibits NOS by substrate depletion (Morris, S. M., Jr. *Annual Review of Nutrition* 22, 87-105 (2002); Mills, C. D. *Crit Rev Immunol* 21, 399-425 (2001)).

In addition, due to the discovery that arginase I and arginase II are upregulated during asthma, it is possible to target drugs to a variety of reactants and products in the arginase pathway to provide a treatment for asthma and allergies. For example, the downstream products of arginase are polyamines and proline which regulate cell growth and connective tissue remodeling. These pathways are known to be involved in the pathophysiology of asthma. Inhibiting any part of the arginase pathway is likely to inhibit the asthma or allergies.

Arginase I mRNA in situ Hybridization

In order to begin to address the cellular sources of these molecules, mRNA in situ hybridization for arginase I was performed, as show in Example 7 below. The hybridization signal of the arginase I antisense (AS) and sense (S) probes was determined for OVA/alum sensitized mice challenged with two doses of OVA or Saline. Tissue was analyzed 18 hours after the second saline or allergen challenge. Antisense staining of asthmatic lung revealed strong levels of arginase I in the perivascular and peribronchial pockets of inflammation. No specific staining with the sense probe in OVA challenged mice was seen. Hybridization of the antisense and sense probes in saline challenged lung was comparable to background. There was a specific staining of the antisense probe to a sub-population of large mononuclear cells with abundant cytoplasm most consistent with macrophages. A sub-population of eosinophils expressed arginase I to a lesser extent. In addition, the antisense probe hybridized to alveolar macrophages and submucosal spindle shaped cells (consistent with myofibroblasts or smooth muscle cells).

Treatment or Prevention of Asthma or Allergies by Administering Compositions that Decrease or Inhibit Arginase in the Lung One embodiment of the invention is a method for inhibiting asthma by administering to an individual in need of treatment therefore a therapeutically effective amount of an arginase inhibitor (Examples 15-20). For example, the L-Arginine transporter CAT2 and L-ornithine decarboxylase (ODC), an enzyme downstream from Arginase, are targets for therapeutic treatment. Difluoromethylornithine (DFMO), for example, which is an inhibitor of ODC, could be a useful treatment for inhibiting asthma or allergy (Examples 17-19). Therefore, an embodiment of the invention is the treatment of asthma or allergy with difluoromethylornithine (DFMO), a known inhibitor of ornithine decarboxylase (ODC). Further embodiments of the invention include the administration of an effective dose of DFMO to an individual suffering from asthma or allergy.

As used herein, anti-arginase compounds are compounds that inhibit or reduce the effect of arginase. In one embodiment, the arginase inhibitor is a small molecule or an antisense inhibitor of a gene involved in the arginase pathway.

In another embodiment of the invention, the arginase inhibitor is an arginase I or an arginase II inhibitor. The arginase inhibitor is preferably administered to the lung of the individual but other modes of treatment are anticipated. Preferable inhibitors of arginase are small molecules, such as, for example, N(omega)-hydroxy-L-arginine (NOHA), N-hydroxy-nor-L-arginine, (nor-NOHA) and boronic acid based transition state analogues such as 2(S)-amino-6-boronohexanoic acid (ABH) and S-(2-boronoethyl)-L-cysteine (BEC). Other inhibitors are described by Que. et al. (*Nitric Oxide.* 2002 Feburary; 6(1):1-8). As indicated in Example 15, it appears that NOHA blocks arginase activity in the asthmatic lung and in Example 20, it blocks the development of allergen-induced airway hyperesponsiveness. Thus, one embodiment of the invention is the treatment of asthma by administration of a therapeutically effective amount of NOHA.

In addition, some of the NO synthase inhibitors block the arginine transporter CAT2 and thus are anticipated to reduce the effects of asthma by lowering the available levels of arginine. Accordingly, an embodiment of the invention is the treatment of asthma or allergy by administering to an individual with asthma or allergies an effective dose of a compound that reduces the level or function of Arg I, Arg II, or CAT2 in the individual.

Another embodiment of the invention is a therapeutic composition for the treatment of asthma or allergies, comprising an arginase inhibitor in a pharmaceutically acceptable carrier. Other embodiments include inhibitors therapeutic compositions comprising ADAM8 inhibitors in a pharmaceutically acceptable carrier. Such inhibitors of ADAM8 can change the conformation or structure of ADAM8 by, for example, converting ADAM8 from a transmembrane to a soluble form.

As used herein the term "treat" or "treatment" refer to both therapeutic treatment and prophylactic or preventative measures wherein the object is to prevent or slow down (lessen) an undesired physiological change or disorder, such as the development or spread of cancer. The term "treat" also refers to the characterization of the type or severity of disease which may have ramifications for future prognosis, or need for specific treatments. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

Therapeutic formulations of the anti-arginase or anti-ADAM8 compounds are prepared for storage by mixing anti-arginase compounds having the desired degree of purity with optional physiologically acceptable carriers, excipients, or stabilizers (*Remington: The Science and Practice of Pharmacy,* 19th Edition, Alfonso, R., ed, Mack Publishing Co. (Easton, Pa.: 1995)), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

An anti-arginase, anti-CAT2, or anti-ADAM8 compound to be used for in vivo administration must be sterile. This is readily accomplished by filtration through sterile filtration membranes, prior to or following lyophilization and reconstitution. The compound ordinarily will be stored in lyophilized form or in solution.

Therapeutic anti-arginase, anti-CAT2, or anti-ADAM8 compounds generally are placed into a container having a sterile access port, for example, an intravenous solution bag or vial having a stopper pierceable by a hypodermic injection needle.

The route of compound administration is in accord with known methods, e.g. injection or infusion by intravenous, intraperitoneal, intracerebral, subcutaneous, epicutaneous, intranasal, intratracheal, nebulized, intramuscular, intraocular, intraarterial, intracerebrospinal, or intralesional routes, or by sustained release systems as noted below.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., *Biopolymers,* 22: 547-556 (1983)), poly (2-hydroxyethyl-methacrylate) (Langer et al., *J. Biomed. Mater. Res.,* 15: 167-277 (1981) and Langer, *Chem. Tech.,* 12: 98-105 (1982)), ethylene vinyl acetate (Langer et al., supra) or poly-D-(-)-3-hydroxybutyric acid (EP 133,988). Sustained-release compounds may also include liposomally entrapped compositions. Liposomes containing compound are prepared by methods known per se: DE 3,218,121; Epstein et al., *Proc. Natl. Acad. Sci. USA,* 82: 3688-3692 (1985); Hwang et al., *Proc. Natl. Acad. Sci. USA,* 77: 4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamelar type in which the lipid content is greater than about 30 mol. % cholesterol, the selected proportion being adjusted for the optimal therapy.

Anti-arginase, anti-CAT2, or anti-ADAM8 compounds can also be administered by inhalation. Commercially available nebulizers for liquid formulations, including jet nebulizers and ultrasonic nebulizers are useful for administration. Liquid formulations can be directly nebulized and lyophilized powder can be nebulized after reconstitution. Alternatively, these compounds can be aerosolized using a fluorocarbon formulation and a metered dose inhaler, or inhaled as a lyophilized and milled powder.

An "effective amount" of a compound to be employed therapeutically will depend, for example, upon the therapeutic objectives, the route of administration, the type of compound employed, and the condition of the patient. Accordingly, it will be necessary for the therapist to titer the dosage and modify the route of administration as required to obtain the optimal therapeutic effect. Typically, the clinician will administer the compound until a dosage is reached that achieves the desired effect. The progress of this therapy is easily monitored by conventional assays.

In the treatment and prevention of asthma or allergies by an anti-arginase, anti-CAT2, or anti-ADAM8 compound, the compound will be formulated, dosed, and administered in a fashion consistent with good medical practice. Factors for consideration in this context include the level of asthma/allergy being treated, the clinical condition of the individual patient, the site of delivery of the compound, the particular type of compound, the method of administration, the scheduling of administration, and other factors known to medical practitioners. The "therapeutically effective amount" of such a compound to be administered will be governed by such considerations, and is the minimum amount necessary to prevent, ameliorate, or treat asthma. Such amount is preferably below the amount that is toxic to the host or renders the host significantly more susceptible to infections.

As a general proposition, the initial pharmaceutically effective amount of the anti-arginase or anti-ADAM8 compound administered parenterally will preferably be in the range of about 0.1 to 50 mg/kg of patient body weight per day, with the typical initial range of compound used being preferably 0.3 to 20 mg/kg/day, and more preferably 0.3 to 15 mg/kg/day. The desired dosage can be delivered by a single bolus administration, by multiple bolus administrations, or by continuous infusion administration of the compound, depending on the pattern of pharmacokinetic decay that the practitioner wishes to achieve.

As noted above, however, these suggested amounts of compound are subject to a great deal of therapeutic discretion, including the individual type of compound being used. The key factor in selecting an appropriate dose and scheduling is the result obtained, as indicated above. For example, the compound may be optionally formulated with one or more agents currently used to prevent or treat asthma. The effective amount of such other agents depends on the amount of the compound present in the formulation, the clinical level of the asthma, and other factors discussed above. These are generally used in the same dosages and with administration routes as used hereinbefore or about from 1 to 99% of the heretofore employed dosages.

Treatment of Asthma or Allergies by Increasing Arginase in Particular Tissues while Decreasing Arginase in Other Tissues Yet another embodiment of the invention includes increasing the levels of arginase in particular tissues of a patient in order to provide a protective response. This relates to the fact that increasing arginase will decrease NO production by functionally (directly or indirectly) inhibiting NO synthase. Because NO oxidative products induce a variety of inflammatory responses, arginase production in the lung may be protective in terms of decreasing NO-dependent inflammation, but damaging in terms of chronic changes in the lung (e.g. smooth muscle cell growth and fibrosis). One embodiment of the invention includes administering to a patient a compound that increases arginase in specific cell types in the lung (macrophages), but decreases arginase in other cells (endothelial cells, fibroblasts, smooth muscle) in the lungs.

Screening for Molecules that Interact or Bind with the Arginase I, Arginase II, CAT2, or ADAM8 Genes Or Proteins Other embodiments of the present invention provide methods of screening or identifying proteins, small molecules or other compounds which are capable of inducing or inhibiting the expression of the arginase I genes and proteins. The assays may be performed in vitro using transformed or non-transformed cells, immortalized cell lines, or in vivo using transformed mammalian cells. In particular, the assays may detect the presence of increased or decreased expression of arginase I genes or arginase I proteins on the basis of increased or decreased mRNA expression, increased or decreased levels of arginase I protein, or increased or decreased levels of expression of arginase pathway products such as putrescine or ornithine. Additionally, biological fluid from the respiratory tract (e.g. lung extracts, sputum, bronchoalveolar lavage fluid) or blood samples (white blood cells) can be assayed for arginase activity and then screened for inhibitors of this enzymatic activity.

For example, isolated cells known to express arginase I polypeptide, or transformed to express an arginase I polypeptide, are incubated and one or more test compounds are added to the medium. After allowing a sufficient period of time, e.g., anywhere from 0-72 hours, or longer, for the compound to induce or inhibit the expression of arginase I, any change in levels of expression from an established baseline may be detected.

Additional embodiments of the present invention provide methods for identifying proteins and other compounds which bind to, or otherwise directly interact with, the arginase I protein. The proteins and compounds will include endogenous cellular components which interact with arginase I in vivo and which, therefore, provide new targets for pharmaceutical agents, as well as recombinant, synthetic and otherwise exogenous compounds which may have arginase I binding capacity and, therefore, may be candidates for inhibiting the asthma response.

Thus, in one series of embodiments, high throughput screen (HTS) protein or DNA chips, cell lysates or tissue homogenates may be screened for proteins or other compounds which bind to the arginase I gene/protein, arginase II gene/protein, Cat2 gene/protein, or ADAM8 gene/protein Alternatively, any of a variety of exogenous compounds, both naturally occurring and/or synthetic (e.g., libraries of small molecules or peptides), may be screened for arginase I binding capacity.

In various embodiments, an assay is conducted to detect binding of arginase I, arginase II, cat2, ADAM8 and another moiety. The arginase I, arginase II, cat2, ADAM8 in these assays may be any polypeptide comprising or derived from a normal or mutant arginase I protein, including functional domains or antigenic determinants of arginase I, arginase II, cat2, or ADAM8 fusion proteins. Binding may be detected by non-specific measures (e.g., transcription modulation, altered chromatin structure, peptide production or changes in the expression of other downstream genes which can be monitored by differential display, 2D gel electrophoresis, differential hybridization, or SAGE methods) or by direct measures such as immunoprecipitation, the Biomolecular Interaction Assay (BIAcore) or alteration of protein gel electrophoresis. The preferred methods involve variations on the following techniques: (1) direct extraction by affinity chromatography; (2) co-isolation of arginase I components and bound proteins or other compounds by immunoprecipitation; (3) BIAcore analysis; and (4) yeast two-hybrid systems.

Additional embodiments of the present invention provide methods of identifying proteins, small molecules and other compounds capable of modulating the activity of normal or mutant arginase I, arginase II, cat2, or ADAM8.

Additional embodiments of the present invention provide methods of identifying compounds on the basis of their ability to affect the expression of arginase I, arginase II, cat2, or ADAM8, the activity of arginase I, the activity of other arginase I-regulated genes, or the activity of proteins that interact with normal or mutant arginase I proteins. Methods of identifying compounds with activity toward the arginase I gene or the arginase I protein may be practiced using normal cells, or recombinant cells, or using the murine experimental asthma models as herein described.

In accordance with another aspect of the invention, the proteins of the invention can be used as starting points for rational chemical design to provide ligands or other types of small chemical molecules. Alternatively, small molecules or other compounds identified by the above-described screening assays may serve as "lead compounds" in design of modulators of arginase I pathways in mammals.

Detection and Quantitation of Arginase can be used to Diagnose Asthma or Allergies in a Patient Another embodiment of the invention is a method for detecting asthma in an individual by measuring the level of arginase in the individual's biological fluid/tissue (e.g. lung, sputum, bronchoalveolar fluid, blood, plasma, urine, or nasal secretions/washes). Levels of arginase that are greater than normal are indicative that the individual has asthma. In addition, the levels of arginase may be a phenotypic marker with diagnostic value. For example, patients with elevated arginase activity, may have a stronger likelihood of allergic etiology, recent allergen exposure, or disease severity.

Relationship Between Cytokines and Arginase I Induction

As discussed above, embodiments of the invention relate to the discovery that the enzymes Arginase I and Arginase II are strongly upregulated during asthma, as shown in Example 8 below. Arginase catalyzes the reaction L-Arginine+$H_2O$->L-Ornithine+Urea. As is known, arginase participates in the Krebs-Henseleit urea cycle and is most highly concentrated in mammalian liver.

However in addition, it was discovered that lung Arginase I was markedly induced by the cytokines Interleukin-4 (IL-4) and Interleukin-13 (IL-13) in a Signal-Transducer-and-Activator-of-Transcription 6 (STAT-6) dependent manner. As discussed above, both IL-4 and IL-13 have been found to play a role in activating the inflammatory and residual effector pathways that result in clinical asthma and allergic indications, as indicated below in Example 9. Thus, drugs that block IL-4, IL-13, STAT6 are likely to reduce levels of arginase, and thus be a treatment for patients afflicted by asthma or allergies. As a corollary, decreases in arginase activity in biological fluids such as blood, sputum, lung fluid, biopies, at the like, may be an indication of positive responses to drugs such as glucocorticoids or anti-IL4, anti-IL-13, or anti-STAT6 compounds.

Allergic Airway Inflammation is Associated with Increased Production of Lung Putrescine.

Other embodiments of the invention relate to our discovery that allergic responses, mediated by Th2 cytokines, may be associated with marked induction of arginine metabolism via arginase. To demonstrate that products downstream from arginase were actually overproduced in the allergic lung, we analyzed polyamine putrescine, an arginase-dependent metabolite of arginine.

We discovered that OVA challenged mice had significantly increased levels of putrescine (14.7±5.6 vs. 32±13 nmol/g tissue [P<0.05] in saline and OVA, respectively), when whole lung tissue was measured. The 2-fold increase in putrescine is remarkable, considering that the entire lung was measured. Because airway inflammation is linked with increased production of lung putrescine, one embodiment of the invention is decreasing lung levels of putrescine in order to provide an effective treatment for individuals with allergic lungs. Accordingly, one embodiment of the invention is the treatment of an allergic lung with compositions that reduce putrescine levels in the lung. Further, another embodiment of the invention is the detection and/or diagnosis of allergic lung by determining increased putrescine levels in the lung.

Arginase is Induced in Human Asthma

Figure 10:
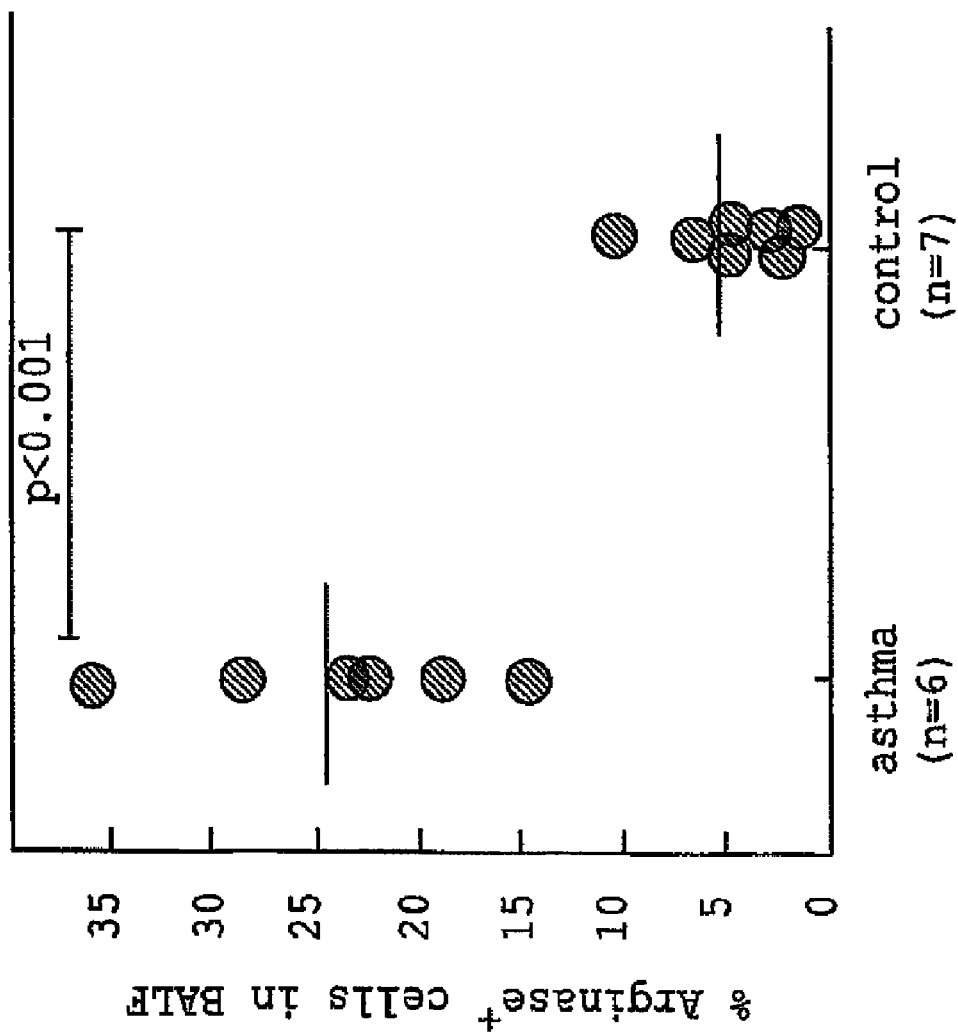
FIG. 10 is a plot illustrating Arginase I protein expression in human asthma. Fiberoptic bronchoscopy of allergic asthmatics and healthy controls was conducted, and BALF was analyzed for arginase I immunohistochemistry. The number of immunopositive cells, expressed as a percentage of total cells, is shown.

The findings from the experimental asthma model in mice were found to correlate with human asthma (FIG. 10). To translate the mouse model results into humans, arginase I protein expression in bronchoalveolar lavage fluid cells was analyzed from individuals with asthma and from control patients (Example 13). Using immunocytochemistry, there was a significantly higher number of cells expressing arginase I in the asthmatic group (FIG. 10).

In both groups, the immunopositive cells were predominantly mononuclear cells with macrophage morphology. A small population of immunopositive granulocytes was present in the asthmatic group. Additionally, in situ hybridization with arginase I sense probes revealed elevated levels of arginase I mRNA expression in the asthmatic lung compared with non-asthmatic lungs (control). Arginase I+ cells in the asthmatic lung included epithelial cells, as well as submucosal cells including smooth muscle and infiltrative myeloid cells.

CAT2 is Involved in Diverse Processes in Experimental Asthma.

Another embodiment of the invention relates to the discovery that the amino acid transporter CAT2 is also involved in asthma pathogenesis through the arginase pathway. In order to determine which isoform of CAT was expressed in the asthmatic lung, we cloned lung CAT2 cDNA by PCR (FIG. 9).

Figure 9:
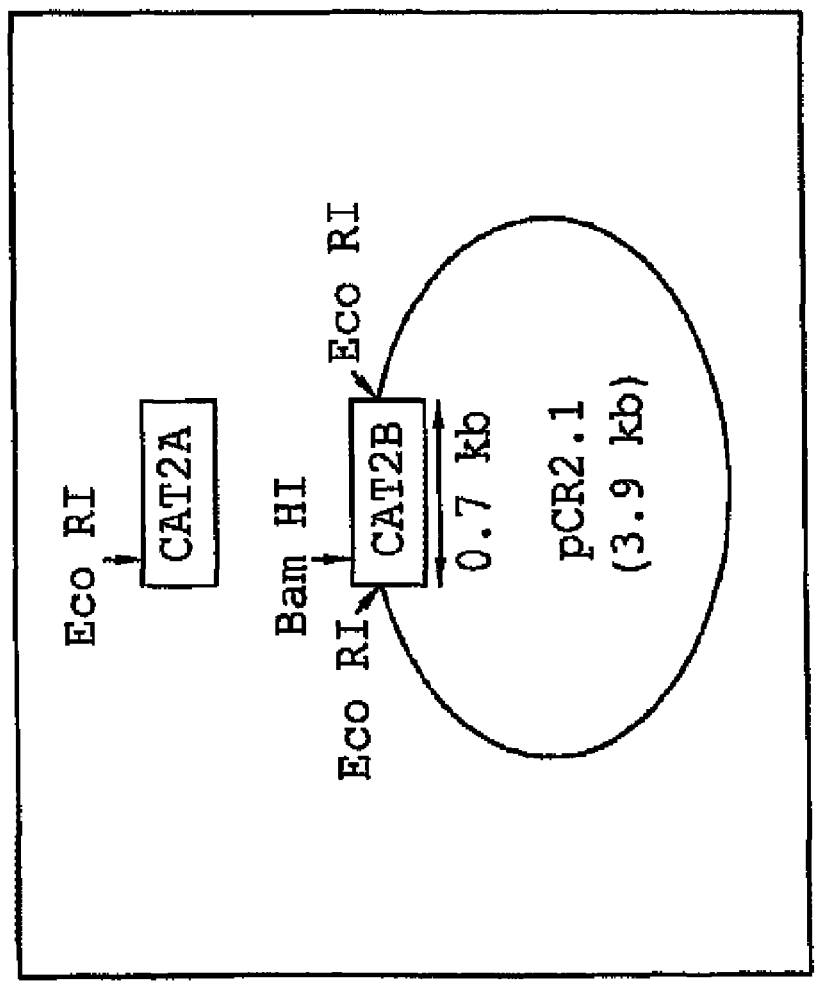
FIG. 9 is a schematic representation of the method used to determine involvement of CAT2 (and in particular, CAT2A versus CAT2B isoforms) in experimental asthma. CAT2 was amplified by RT-PCR from lungs of allergen-challenged mice and subcloned into the pCR2.1 vector. Subsequently, clones were digested with EcoRI or EcoRI/BamHI in order to differentiate CAT2A and CAT2B subtypes, respectively.

We subsequently cloned the PCR product in a TA-vector (pCR2. 1, Invitrogen, Inc) and digested the inserts with EcoRI (that specifically digests in exon 8) and with BamHI (that specifically digests in exon 7) (FIG. 9). All clone inserts analyzed (n=6) liberated the expected digestion products with BamHI, but were not digested with EcoRI. As a control, cDNA derived from the liver, liberated the expected 4 kb vector and the 600 and 100 bp insert products following digestion with EcoRI alone, indicative of the CAT2A isoform. These results indicated that CAT2 in the allergic lung was primarily the high affinity CAT2B isoform.

Macrophages from CAT2 deficient mice have been shown to have a 95% decrease in L-arginine uptake and a marked impairment in NO production (Nicholson et al., *J Biol Chem*, 276:15881-5 (2001)). In order to examine the role of CAT2 in experimental asthma, CAT2 deficient mice (and their littermate controls) were subjected to the OVA-induced experimental asthma regime. Microarray analysis was used to screen for a large set of potential endpoints, analyzing transcript profiles from these mice following allergen challenge. Notably, compared with wild type mice, CAT2 deficient mice had decreased levels of 6.8% of the allergen-induced gene products. One of these products was CAT2 itself, validating the genomic analysis. Interestingly, CAT2 deficient mice had impaired induction of molecules known to be critical in allergic airway responses including the chemokine TARC (Lloyd et al., *J Exp Med.* 191:265-74 (2000); Kawasaki et al., *J Immunol,* 166:2055-62 (2001)) and the enzyme 15-lipoxygenase (Sigal et al., *J Lipid Mediat,* 6:75-88 (1993); Kuitert et al., *Thorax,* 51:1223-8 (1996); Bradding et al., *Am J Respir Crit Care Med.* 151:1201-4 (1995)). Additionally, the CAT2 deficient mice had impaired induction of small proline rich (SPR) protein 2A, an epithelial secreted molecule known to be important in extracellular matrix integrity (Cabral et al., *J Biol Chem,* 276:19231-7 (2001); De Heller-Milev et al., *Br J Dermatol,* 143:733-40 (2000)). For each gene, Northern blot analysis was used to confirm that CAT2 was indeed required for proper induction by allergen.

Although CAT2 was originally described as a T cell activation molecule, its role in T cell-mediated immune responses has not been previously reported (MacLeod et al., *J Exp Biol,* 196:109-21 (1994)). The first indication that CAT2 may be involved in critically regulating substrate availability for iNOS or arginase was the findings that pro-inflammatory molecules (e.g. lipopolysaccharide) regulate CAT2 expression (MacLeod et al., *J Exp Biol,* 196:109-21 (1994)). The recent finding that CAT2 deficient macrophages have a marked impairment of arginine uptake and NO production has solidified a role for CAT2 in immunological responses (Nicholson et al., *J Biol Chem,* 276:15881-5 (2001)). While amino acid transport by CAT2 is likely to have an impact on a number of biochemical pathways associated with asthma, microarray analysis was used to determine if CAT2 affects gene expression in the asthmatic lung. Indeed, we demonstrated that impairment in a select subpopulation of allergen-induced genes, including TARC and 15-lipoxygenase, genes that encode for proteins already demonstrated to be involved in some aspects of allergic airway responses (Kawasaki et al., *J ImmunolI,* 166:2055-62 (2001); Sigal et al., *J Lipid Mediat,* 6:75-88 (1993); Bradding et al., *Am J Respir Crit Care Med.* 151:1201-4 (1995)). CAT2 may regulate gene expression and play a role in asthma by a number of mechanisms including direct effects on transcription, or alternatively via indirect effects mediated by a cascade of downstream biochemical signaling events.

Methods that Decrease or Inhibit CAT2 in the Lung may be Useful to Treat or Prevent Asthma or Allergies Because of this role of CAT2 in asthma, it may be useful to treat asthma or allergies with compositions that are capable of decreasing or inhibiting CAT2 in the lung. This may be accomplished, for example, by administering CAT2 inhibitors to the lung. This may also be accomplished by administering antisense fragments of the CAT2 gene sequences, or by administering a nucleic acid vector sequence that is capable of delivering such antisense fragments to the lung. Any method that is capable of decreasing CAT2 expression or function may be useful for the treatment of asthma or allergies.

Treatment of Asthma or Allergies by Increasing CAT2 in Particular Tissues

Yet another embodiment of the invention includes increasing the levels of CAT2 in particular tissues of a patient in order to provide a protective response related to the production of the bronchodilator NO by eNOS. This relates to the fact that increasing CAT2 levels or function will increase NO production. One embodiment of the invention includes administering to a patient a compound that increases CAT2 in specific cell types in the lung (e.g. endothelial cells), but decreases arginase in other cells in the lungs.

Relationship of ADAM-8 to Asthma

Another embodiment of the invention relates to the discovery that induction of ADAM-8, also known as CD156, was shown to occur in a distinct model of asthma that was induced by repeated mucosal allergen challenges with the aeroallergen *Aspergillus fumigatus*. Having identified ADAM-8 as part of the genetic program associated with antigen induced airway inflammation, it was relevant to dissect the signals that were specifically involved in regulating its expression. The expression of ADAM-8 was strongly increased by IL-4 and IL-13 delivery to the lungs, and its induction was largely independent of signal-transducer-and-activator-of-transcription (STAT)-6. Thus, treatments which reduce the level of ADAM-8 in a patient are anticipated to provide a therapeutic benefit. In addition, asthma and allergy can be diagnosed in a patient by looking for increased levels of ADAM-8, wherein such increased levels are indicative of asthma or allergy.

ADAM-8 belongs to the ADAM (a disintegrin and metalloprotease) family of type I transmembrane proteins (Yamamoto, S., Higuchi, Y., Yoshiyama, K., Shimizu, E., Kataoka, M., Hijiya, N., and Matsuura, K. 1999. ADAM family proteins in the immune system. *Immunol Today* 20:278-284). While ADAMs 1 through 7 are mainly expressed in the reproductive organs and appear to play a role in sperm-egg fusion and spermatogenesis, other members of this family are more widely expressed. A role for specific members of the ADAM family (ADAM-10 and ADAM-17) has been demonstrated in the immune system where they are involved in processing of the cell surface precursor form of TNF-α. A role for ADAM-8 in the immune system is also likely. This protein was identified from a macrophage cDNA library and has since been documented in PMNs and macrophages in mouse and human (Yoshiyama, K., Higuchi, Y., Kataoka, M., Matsuura, K., and Yamamoto, S. 1997. CD156 (human ADAM8): expression, primary amino acid sequence, and gene location. *Genomics* 41:56-62). A transgenic mouse expressing the extracellular portion of ADAM-8 in liver and kidneys demonstrated neutrophil infiltration following oxazolone-mediated contact hypersensitivity. It has also been demonstrated that ADAM-8 gene expression is upregulated by LPS and IFN-γ (Kataoka, M., Yoshiyama, K., Matsuura, K., Hijiya, N., Higuchi, Y., and Yamamoto, S. 1997, Structure of the murine CD156 gene, characterization of its promoter, and chromosomal location. *J. Biol. Chem.* 272:18209-18215).

However, the role of ADAM-8 in allergic responses has previously not been established. Although the above-described microarray contained 18 members of the ADAM family, there was only one ADAM gene that was significantly induced. This gene was reproducibly identified at high levels in each of the allergen treated mice compared with saline treated mice. In addition, because members of the ADAM family of type I transmembrane proteins have been implicated in regulating immune responses (e.g. proteolytic processing of the cell surface TNF-αprecursor) (Black, R. A., Rauch, C. T., Kozlosky, C. J., Peschon, J. J., Slack, J. L., Wolfson, M. F., Castner, B. J., Stocking, K. L., Reddy, P., Srinivasan, S., et al. 1997. A metalloproteinase disintegrin that releases tumour-necrosis factor-alpha from cells. *Nature* 385:729-733), this molecule represented a potentially important novel pathway in experimental asthma. Northern blot analysis was subsequently used to confirm that ADAM-8 was indeed induced by allergen challenge compared to its low level of constitutive expression in the lung, spleen, and testis.

ADAM-8 Induction in a Distinct Asthma Model.

Figure 6:
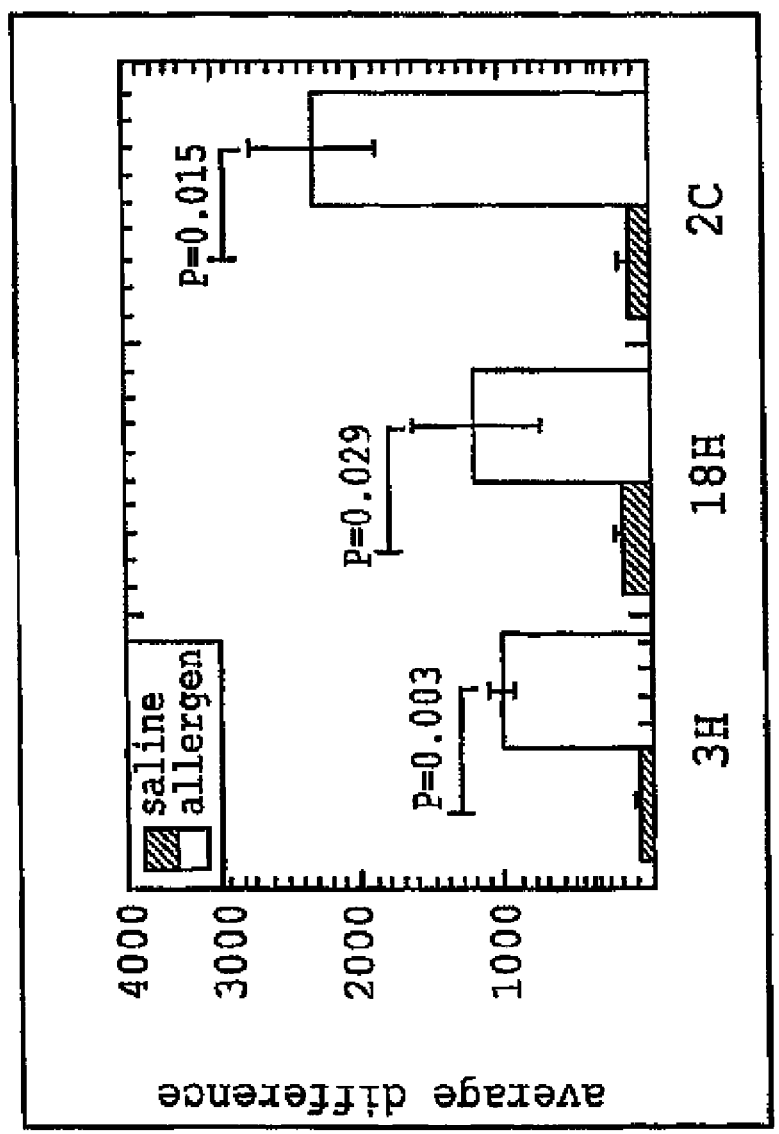
FIG. 6 is a bar graph illustrating the induction of ADAM-8 in allergen-challenged mice, as measured by gene chip analysis. The average difference for the hybridization signal of ADAM-8 following saline (grey bar) and allergen (black bar) challenge is depicted. Error bars represent the standard deviation. Time points are: 3H-1 challenge, 3 hours; 18H-1 challenge, 18 hours; 2C-2 challenges, 18 hours.
Figure 7A:
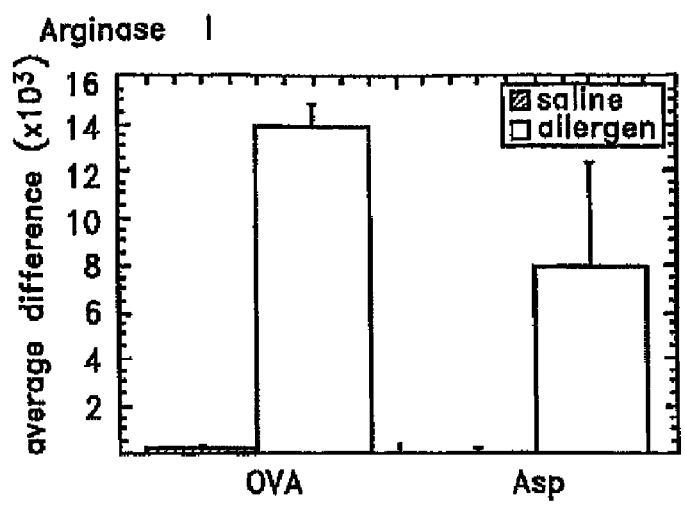
FIG. 7 shows the Expression of L-arginine metabolizing enzymes arginase I (FIG. 7A), arginase II (FIG. 7B), CAT2 (FIG. 7C) in ovalbumin (OVA) and *Aspergillus fumigatus* (Asp)-challenged mice as measured by gene chip analysis. The average difference for the hybridization signal following saline (grey bar) and allergen (black bar) challenge is depicted. Error bars represent the standard deviation.
Figure 7B:
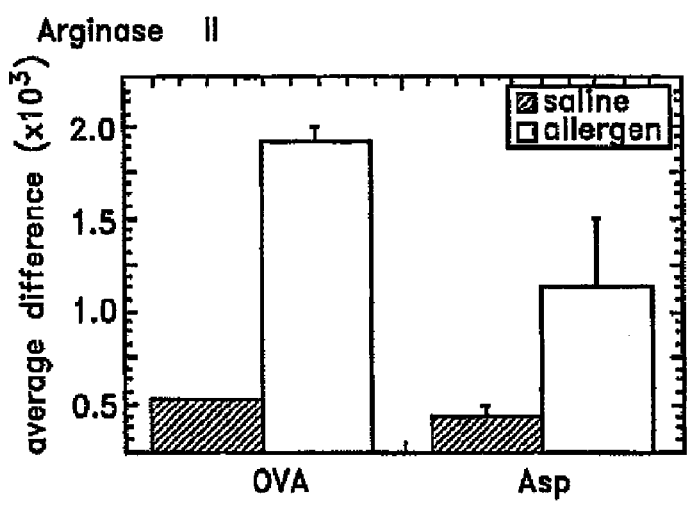
Figure 7C:
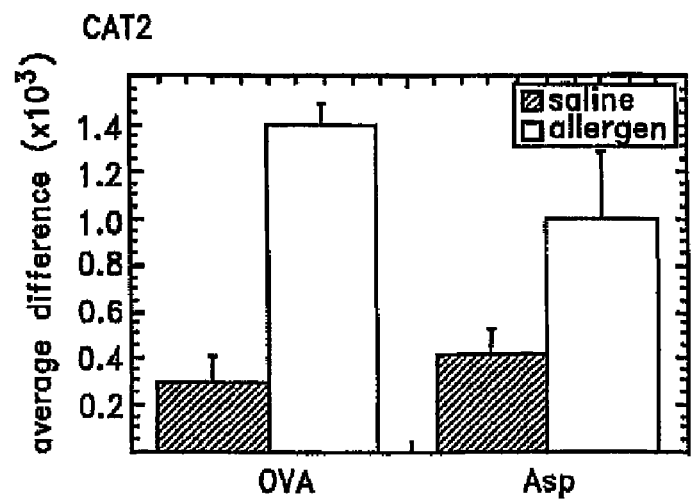

We determined if the association of ADAM-8 with the experimental asthma model was limited to the specific model employed with OVA. Accordingly, we induced experimental asthma by repeated doses of *Aspergillus fumigatus* intranasal antigens (Huang, W. W., Garcia-Zepeda, E. A., Sauty, A., Oettgen, H. C., Rothenberg, M. E., and Luster, A. D. 1998. Molecular and biological characterization of the murine leukotriene $B_4$ receptor expressed on eosinophils. *J. Exp. Med.* 188:1063-1074.). It is noteworthy that this model does not involve intraperitoneal sensitization and that *Aspergillus fumigatus* is a ubiquitous common aeroallergen. Eighteen hours after nine doses of intranasal *Aspergillus fumigatus*, total lung RNA was subjected to Northern blot analysis and probed for ADAM-8. Compared with mice challenged with nine doses of intranasal saline, *Aspergillus fumigatus* challenged mice had marked ADAM-8 mRNA expression. Thus, the induction of ADAM-8 by allergen challenge was not specific to the antigen employed but appeared to be a gene involved in the genetic program of experimental asthma (FIG. 6 and Table 1).

Regulation of ADAM-8 Expression

Having identified ADAM-8 as a novel gene associated with allergic airway responses, we were interested in dissecting the molecules involved in ADAM-8 regulation. Because a central feature of allergic responses is the overexpression of Th2 cytokines such as IL-4 and IL-13, we next determined if these cytokines could directly induce ADAM-8 expression. In order to test this hypothesis, we examined ADAM-8 expression in transgenic mice overexpressing IL-4 specifically in the lung.

Compared to wild type mice, IL-4 lung transgenic mice had markedly elevated levels of ADAM-8 mRNA expression. We next tested the ability of IL-13 delivery to the lungs to induce ADAM-8. Pharmacological delivery of IL-13 to the lung via an intranasal approach induced increased levels of ADAM-8 mRNA compared with saline treated animals. IL-4 and IL-13 share a common receptor signaling pathway that involves post-receptor events that are STAT-6 dependent and independent. We were therefore interested in determining if STAT-6 was required for ADAM-8 induction. In order to test this hypothesis, we examined ADAM-8 expression in IL-4 lung transgenic mice that were STAT-6 wild-type or gene deleted. Interestingly, Northern blot analysis was also used to determine that IL-4 induced ADAM-8 expression was largely STAT-6 independent.

Treatment of Asthma or Allergies by Modulating Levels of ADAM-8 Expression in the Lung Accordingly, another embodiment of the invention is a method of for treating asthma or allergies by administering to a patient a composition that reduces the level of ADAM-8 in the patient. This may be accomplished, for example, by administering ADAM-8 inhibitors to the lung. This may also be accomplished by administering antisense fragments of the ADAM-8 gene sequences, or by administering a nucleic acid vector sequence that is capable of delivering such antisense fragments to the lung. Any method that is capable of decreasing ADAM-8 expression may be useful for the treatment of asthma or allergies. Further, detection and quantitation of variabilities in ADAM-8 levels or gene sequences in a patient may be useful to diagnose the presence or severity of asthma or allergies.

It will be understood by those of skill in the art that numerous and various modifications can be made without departing from the spirit of the present invention. A more complete understanding can be obtained by reference to the following specific examples which are provided herein for purposes of illustration only and are not intended to limit the scope of the invention.

EXAMPLES

Example 1

Experimental Asthma Induction in Mice

Balb/c mice were obtained from the National Cancer Institute (Frederick, Md.) and housed under pathogen-free conditions. Asthma models were induced by intraperitoneal injection with OVA and 1 mg aluminum hydroxide (alum) on days 0 and 14, followed by intranasal OVA or saline challenge (under conditions which promote delivery of the protein to the lung) on days 24 and 27, *Aspergillus fumigatus* antigen induced asthma was induced over the course of three weeks by repeated intranasal application of the protein to anesthetized mice as described in Huang, W. W., Garcia-Zepeda, E. A., Sauty, A., Oettgen, H. C., Rothenberg, M. E., and Luster, A. D. 1998. Molecular and biological characterization of the murine leukotriene $B_4$ receptor expressed on eosinophils. *J. Exp. Med.* 188:1063-1074 and Mishra, A., Weaver, T. E., Beck, D. C., and Rothenberg, M. E. 2001. Interleukin-5-mediated allergic airway inflammation inhibits the human surfactant protein C promoter in transgenic mice. *J. Biol. Chem.* 276:8453-8459.

Example 2

Preparation of RNA and Microarray Hybridization

RNA was extracted using the Trizol reagent as per the manufacturer's instructions. Following Trizol purification, RNA was repurified with phenol-chloroform extraction and ethanol precipitation. Microarray hybridization was performed by the AFFYMETRIX Gene Chip Core facility at Children's Hospital Medical Center. Briefly, RNA quality was first assessed using the Agilent bioanalyzer (Agilent technologies, Palo Alto, Calif.) and only those samples with 28S/18S ratios between 1.3 and 2 were subsequently used. RNA was converted to cDNA with Superscript choice for cDNA synthesis (Invitrogen, Carlsbad, Calif.) and subsequently converted to biotinylated cRNA with Enzo High Yield RNA Transcript labeling kit (Enzo diagnostics, Farmingdale N.Y.). After hybridization to the murine U74Av2 GeneChip (Affymetrix, Santa Clara, Calif.), the gene chips were automatically washed and stained with streptavidin-phycoerythrin using a fluidics system. The chips were scanned with a Hewlett Packard GeneArray Scanner. This analysis was performed with one mouse per chip ($n \geq 3$ for each allergen challenge condition and $n \geq 2$ for each saline challenge condition).

Example 3

Northern Blot and RT-PCR Analysis

RNA was extracted from the lungs of wild-type Balb/c mice, IL-4 Clara cell 10 lung transgenic mice (Rankin et al., *Proceedings of the National Academy of Sciences of the United States of America*, 93:7821-7825 (1996)) containing wild-type or deleted copies of the gene for STAT6 (Shimoda et al., *Nature,* 380:630-3 (1996)), and from the lungs of mice treated with saline or recombinant murine IL-13, as previously reported (Yang et al., *Am J Respir Cell Mol Biol,* 25:522-30 (2001); Pope et al., *J Allergy Clin Immunol,* 108: 594-601 (2001)). The cDNA probes, generated by PCR or from commercially available vectors [Image Consortium obtained from American Tissue Culture Collection, Rockville, Md. or Incyte Genomics, Palo Alto, Calif.], were sequence confirmed, radiolabelled with $^{32}P$, and hybridized using standard conditions. RT-PCR, using standard procedures with gene specific primers, was performed using lung cDNA as template.

Example 4

Data Analysis

From data image files of the gene chips, gene transcript levels were determined using algorithms in the Microarray Analysis Suite Version 4 software (Affymetrix). Global scaling was performed in order to compare genes from chip to chip; thus each chip was normalized to an arbitrary value (1500). Each gene is typically represented by a probe set of 16 to 20 probe pairs. Each probe pair consists of a perfect match oligonucleotide and a mismatch oligonucleotide that contains a one base mismatch at a central position. Two measures of gene expression were used, absolute call and average difference. Absolute call is a qualitative measure in which each gene is assigned a call of present, marginal or absent based on the hybridization of the RNA to the probe set. Average difference is a quantitative measure of the level of gene expression, calculated by taking the difference between mismatch and perfect match of every probe pair and averaging the differences over the entire probe set. Differences between saline and OVA-treated mice were also determined using the GeneSpring software (Silicon Genetics, Redwood City, Calif.). Data for each allergen challenge time point was normalized to the average of the saline-treated mice. Gene lists were created that contained genes with P<0.05 and >2-fold change. GenBank were used for assignment of cDNAs from unknown expressed sequence tags. Functional classifications were based on the Gene Ontology classification [Ashburner, 2000 #2003] obtained through the NetAffx server and public information in GenBank. The significance of differences between the means of experimental groups were analyzed using Student's unpaired t-test. Values were reported as the mean±standard error of the mean (SEM). Differences in mean values were considered significant if P<0.05.

Example 5

Plethysmography Measurements

Airway reactivity to methacholine was assessed in conscious, unrestrained mice by barometric plethysmography, using apparatus and software supplied by Buxco (Troy, N.Y.). This system yields a dimensionless parameter known as enhanced pause (Penh), reflecting changes in wave-form of the pressure signal from the plethysmography chamber combined with a timing comparison of early and late expiration, which can be used to empirically monitor airway function. Measurement was performed as previously described in Yang, M. et al. (*Am J Respir Cell Mol Biol* 25, 522-30 (2001) and Hamelmann, E. et al. *American Journal of Respiratory & Critical Care Medicine* 156, 766-75 (1997).

Briefly, mice were placed in the chamber and baseline reading taken and averaged for 3 minutes. Aerosolized methacholine (concentrations in solution ranging from 3.125 to 50 mg/ml) was then delivered through an inlet into the chamber for 2 min and readings averaged over a period of 3 min after each dose was administered.

Example 6

Measurement of Arginase Activity and Putrescine Levels

Arginase activity was measured using the blood urea nitrogen reagent (Sigma Chemical Company, St. Louis, Mo.) according to established techniques as exemplified in Wei, L. H., et al., *Proc Natl Acad Sci USA* 98, 9260-4. (2001); Li, H. et al. *Am J Physiol Regul Integr Comp Physiol* 282, R64-R69. (2002); Wei, L. H. et al., *Am J Physiol Cell Physiol* 279, C248-56. (2000). To measure levels of putrescine following acid extraction, ion-pair reverse phase high performance liquid chromatography was performed.

Example 7

In situ Hybridization to Localize Arginase I mRNA

To determine the cellular location of the Arginase I mRNA, in situ hybridization was performed. Tissue was analyzed 18 hours after the second saline or allergen challenge. To prepare the probe, the murine arginase I cDNA in plasmid pCMV-SPORTT6 (Incyte Genomics, St. Louis, Mo.) was linearized by EcoRI or NotI digestion. Antisense and sense RNA probes were generated respectively by T7 and T3 RNA polymerase (Riboprobe Gemini Core System II transcription kit; Promega, Madison, Wis.). The radiolabeled [$\alpha^{35}$-UTP] probes were reduced to an average length of 200 bases by controlled alkaline hydrolysis. The hybridization signal of the arginase I antisense (AS) and sense (S) probes was determined for OVA/alum sensitized mice challenged with two doses of OVA or Saline. The hybridized slides were washed under either high-stringency conditions. Hybridization of the antisense and sense probes in saline challenged lung was comparable to background.

Example 8

Analysis of Arginase I Expression

Figure 5B:
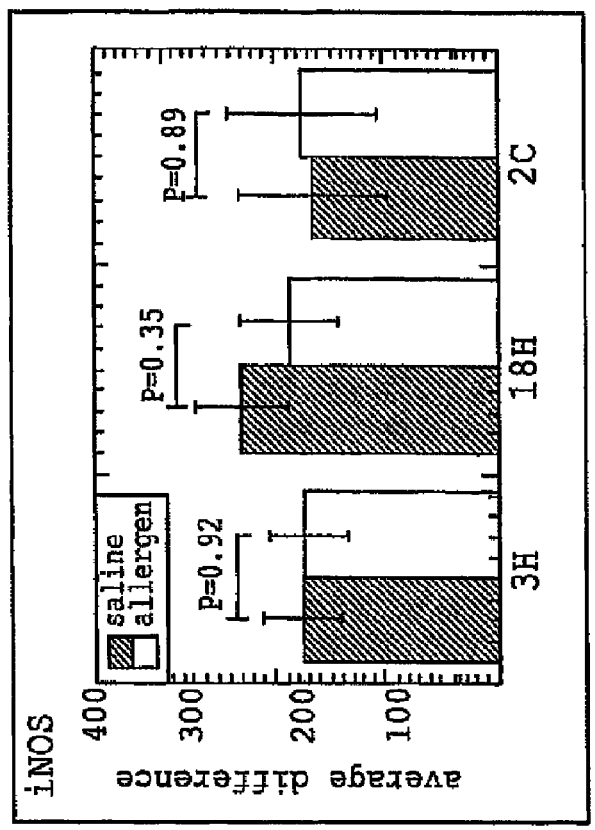
FIG. 5 illustrates the expression of arginine metabolizing enzymes. Expression of arginase I and iNOS in allergen-challenged mice as measured by gene chip analysis is shown in FIGS. 5A and 5B, respectively. The average difference for the hybridization signal following saline (grey bar) and allergen (black bar) challenge is depicted. Error bars represent the standard deviation. Time points are: 3H-1 challenge, 3 hours; 18H-1 challenge, 18 hours; 2C-2 challenges, 18 hours; asp-aspergillus. A schematic representation of the arginine metabolism pathway is shown in FIG. 5C. Genes not present on the gene chip array are depicted with a white box, genes present but not significantly increased with a grey box and significantly increased genes with a black box.
In FIG. 5D, arginase activity in the lungs of saline and OVA-challenged mice is shown. Arginase activity was measured in lung lysates using the blood urea nitrogen reagent. As a control, arginase activity in the liver was 1522±183 and 1390±78 for saline and OVA challenged mice, respectively.
Figure 5A:
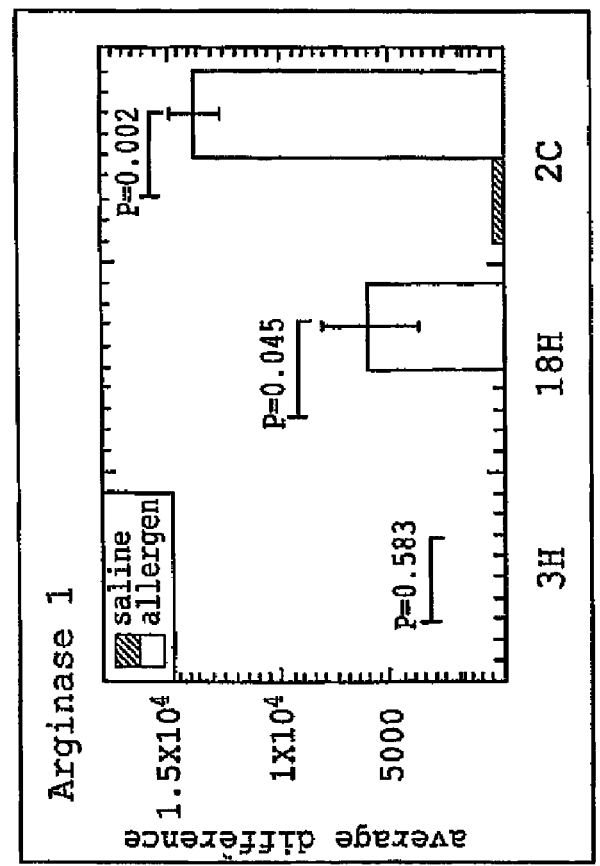
Figure 5C:
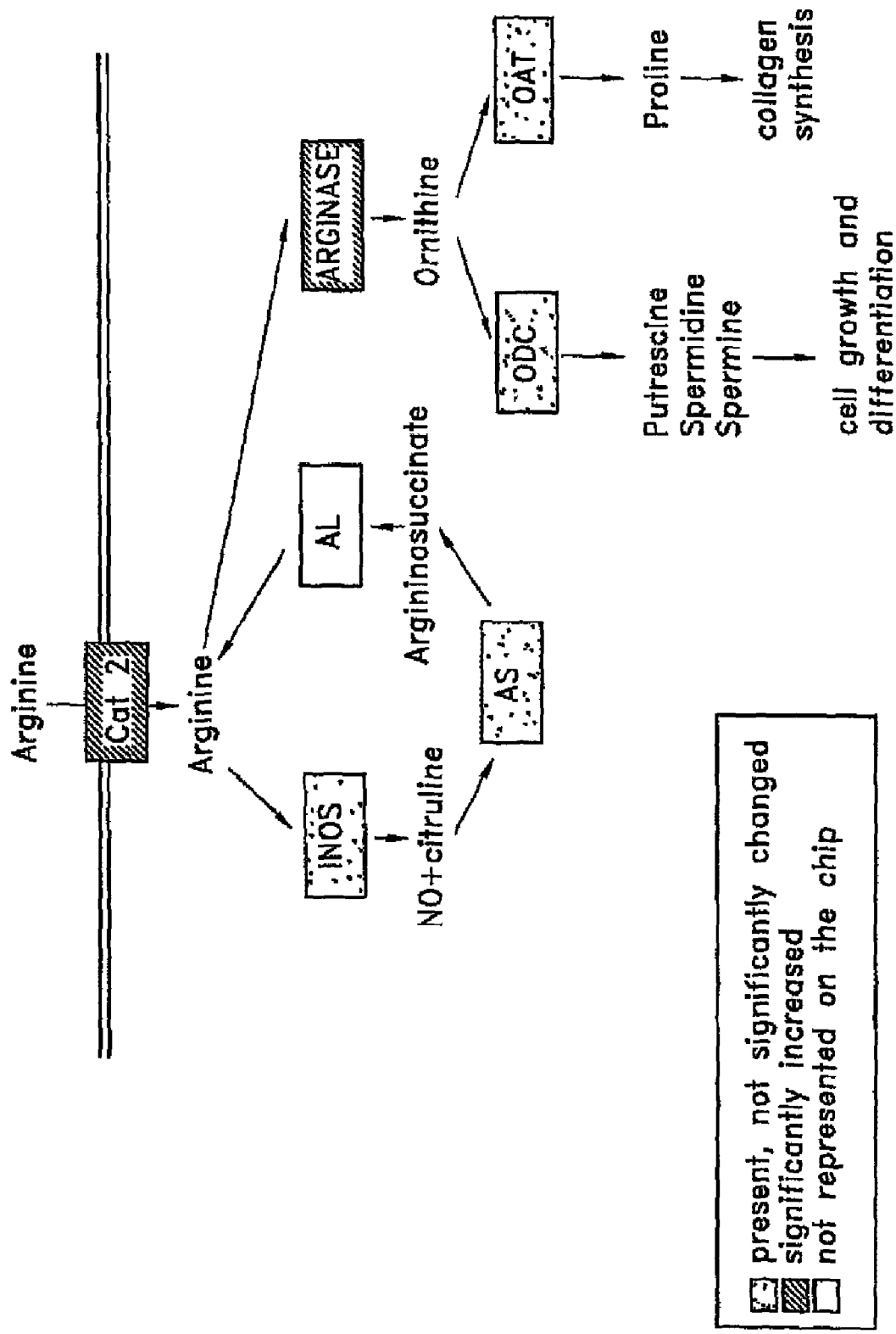
Figure 5D:
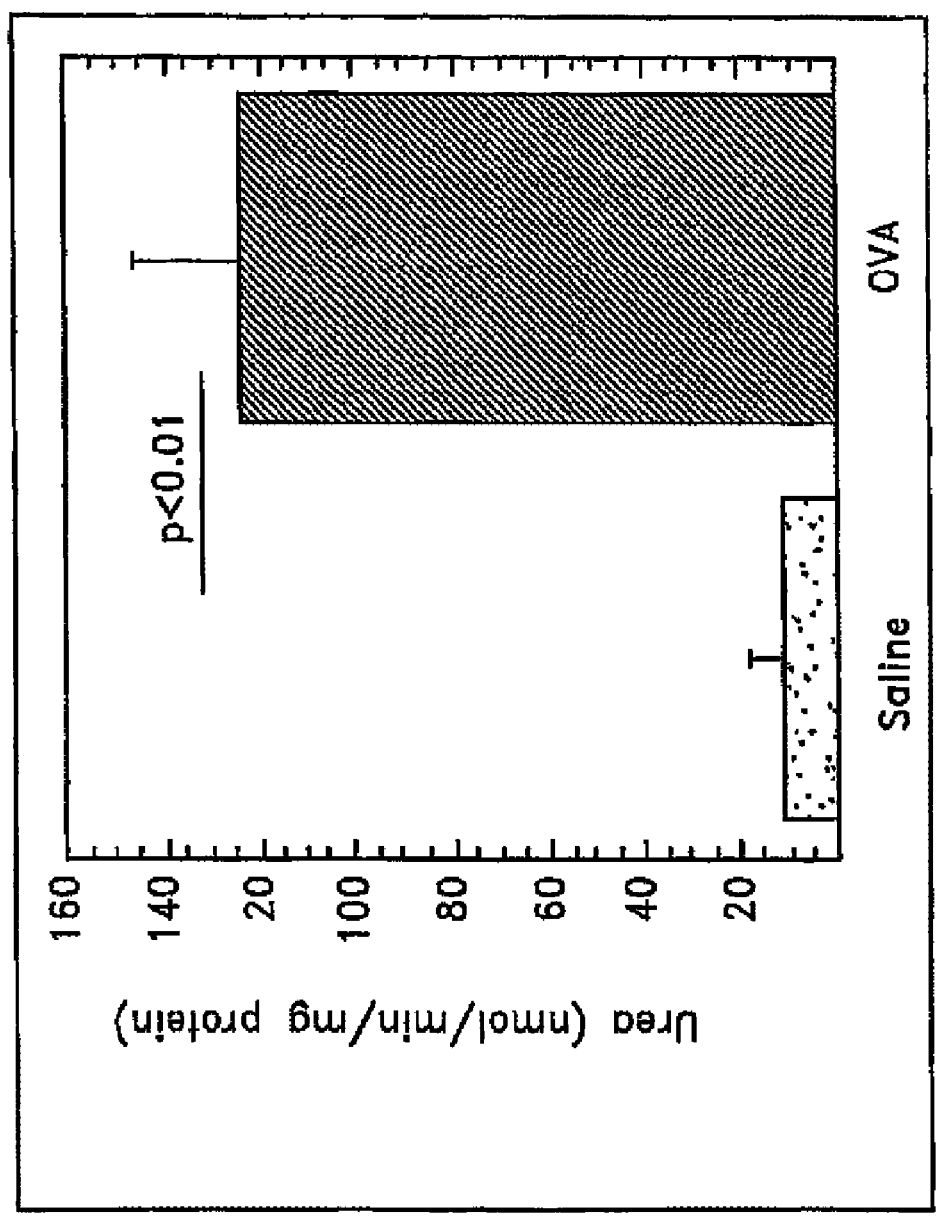

The above-described Gene chip analysis was used to measure expression of genes encoding arginine metabolizing enzymes arginase I and iNOS at three hours after one challenge or at eighteen hours after either one or two challenges. Additionally, Northern blot analysis of arginase I and iNOS expression also revealed that OVA-induced allergy resulted in no noticeable expression of arginase I at three hours, but considerable expression at 18 hours, and a high level of expression at 18 hours when two challenges were initially performed. In contrast, Northern blot analysis of iNOS expression was not visible. Activity of the arginase enzyme activity in the lungs of saline and OVA-challenged mice (FIG. 5D) was measured in lung lysates using the blood urea nitrogen reagent. As a control, arginase activity in the liver was 1522±183 and 1390±78 for saline and OVA challenged mice, respectively.

Example 9

Analysis of Arginase I with Respect to IL-4 and IL-3

In order to elucidate the asthma-associated signals that induce arginase in the lung, the study focused on determining if arginase I was downstream from the Th2 cytokines IL-4 and IL-13. Northern blot analysis of arginase I in IL-4 lung transgenic mice and IL-13 treated lungs was performed. Compared to wild type mice, IL-4 lung transgenic mice expressed markedly elevated levels of arginase I. Furthermore, pharmacological delivery of IL-13 to the lung increased arginase I mRNA compared with saline treated animals. IL-4 and IL-13 share similar signaling requirements in part such as utilization of the IL-4Rα chain and the induction of janus kinase 1 and signal-transducer-and-activator-of-transcription (STAT) 6. In order to determine if arginase I induction was dependent upon STAT6, IL-4 lung transgenic mice containing wild type or gene targeted STAT6 were examined. The IL-4 induced arginase I expression was found to be STAT-6 dependent. Additionally, allergen induced arginase I induction was also found to be STAT-6 dependent.

These studies are consistent with the ability of IL-4 and IL-13 to induce arginase in macrophages in vitro, thereby limiting NOS-dependent NO production. The findings do not negate a role for nitric oxide in asthma, rather we propose that arginine is metabolized largely by arginase in the asthmatic lung. This proposal is supported by the recent observation that NOS and arginase are differentially regulated during Th1 and Th2-associated granulomatous responses in mice, respectively.

Example 10

Overexpression of IL-4 Potently Induces Lung Arginase in vivo

Because asthma is a Th2 associated process and because IL-4 has been shown to induce arginase in several cell lines in vitro (e.g. macrophages, smooth muscle cells) (Munder, M. et al. *J Immunol* 163, 3771-7 (1999); Wei, L. H., et al., *Am J Physiol Cell Physiol* 279, C248-56 (2000)), we were interested in testing the hypothesis that overexpression of IL-4, particularly in the lungs, was sufficient for induction of arginase. Mice that overexpress the IL-4 transgene in pulmonary epithelium (under the control of the Clara cell 10 promoter) have several features of asthma including eosinophil-rich inflammatory cell infiltrates, mucus production, and changes in baseline airway tone (Rankin, J. A. et al. *Proc. Nat. Acad. Sci. U.S.A.* 93, 7821-7825 (1996)). We hypothesized that arginase mRNA would be induced by the IL-4 transgene. Indeed, IL-4 lung transgenic mice had a marked increase mRNA levels of both arginase isotypes. Additionally, CAT2 was also induced in the IL-4 lung transgenic mice.

Example 11

IL-13 Rapidly Induces Arginase in a Time Frame that Correlates with Airway Hyperresponsiveness (AHR).

To determine if lung arginase was also induced by IL-13, (a cytokine that has been shown to be critically involved in the development of several features of experimental asthma (Wills-Karp, M., *J Allergy Clin Immunol* 107, 9-18 (2001); Grunig, G. et al. *Science* 282, 2261-3 (1998)), and to induce arginase in cell lines in vitro (Wei, L. H., et al., *Am J Physiol Cell Physiol* 279, C248-56 (2000); Rutschman, R. et al. *J Immunol* 166, 2173-7 (2001)), we administered IL-13 by repeated intranasal application to anesthetized mice. This protocol induces several features of experimental asthma including eosinophilic inflammation, chemokine induction, mucus production, and AHR (Grunig, G. et al. *Science* 282, 2261-3 (1998); Yang, M. et al. *Am J Respir Cell Mol Biol* 25, 522-30 (2001)). IL-13 administration induced marked levels of arginase I mRNA compared with saline treated control mice. Consistent with the finding that IL-4 transgenic mice had elevated levels of arginase II mRNA, IL-13 also increased arginase II mRNA levels.

Figure 8A:
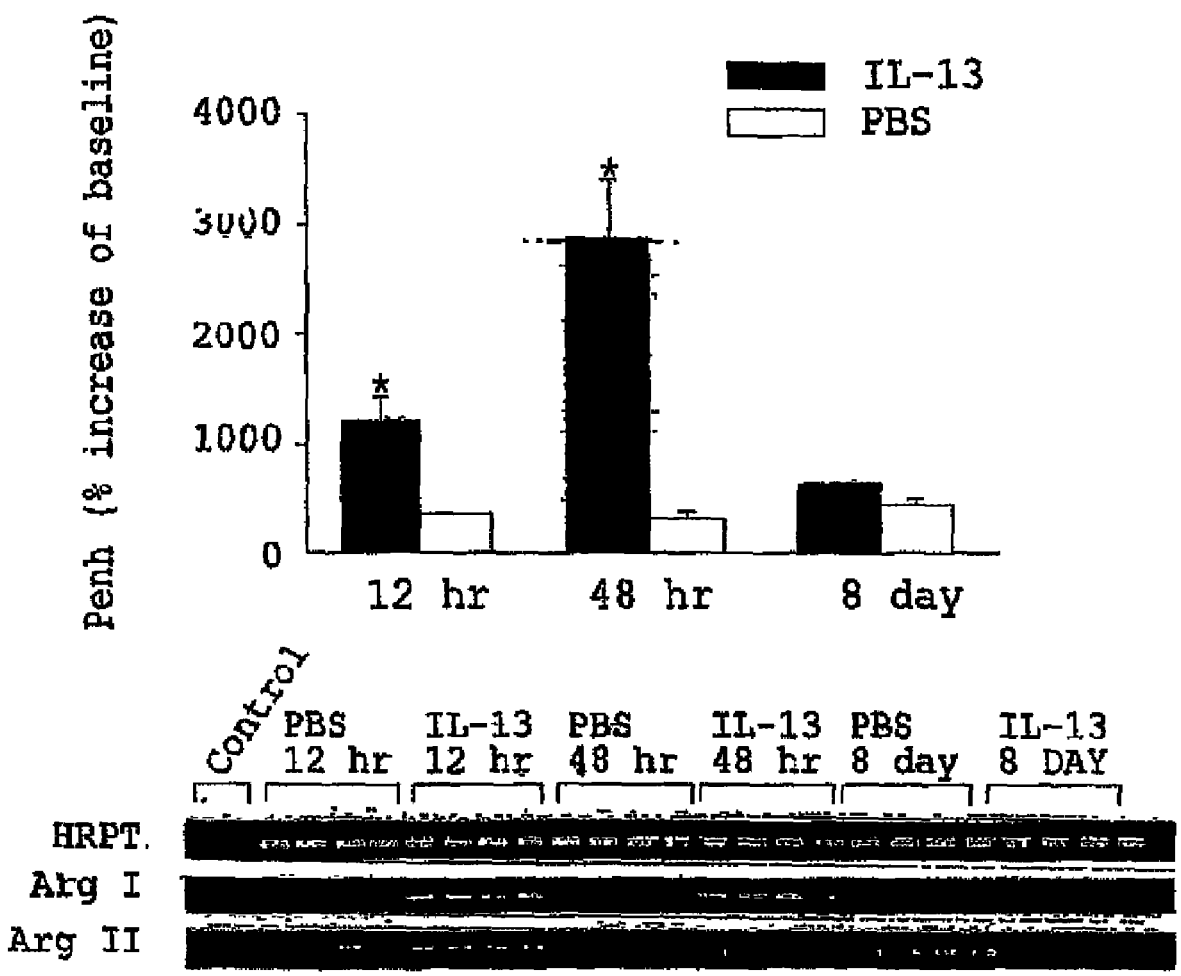
FIG. 8A is a bar graph showing a kinetic characterization of IL-13 induced airway hyperresponsiveness (AHR) and arginase mRNA levels in the lung. Mice (n=4–10/group) received one dose of intratracheal IL-13 (10 µg) or PBS and were analyzed at various time points for AHR, reported as Penh (for 25 mg/ml of methacholine, which gave the maximum response). In the lower panel, lung RNA was converted to cDNA and used for PCR analysis of arginase I (Arg I), arginase II (Arg II), or control hypoxanthine phosphoribosyltransferase (UPRT). The lane labeled "control" does not contain cDNA template.

One dose of intratracheal IL-13 induces marked AHR within 12 hours; IL-13-induced AHR precedes leukocyte recruitment into the airway (Yang, M. et al. *Am J Respir Cell Mol Biol* 25, 522-30 (2001), suggesting that the ability of IL-13 to induce early AHR is dissociated from infiltrating leukocytes. Therefore, a kinetic analysis of IL-13 induction of arginase was performed. Notably, after only one dose of IL-13, the mRNA for the type I isoenzyme was already induced at the 12 hour timepoint (FIG. 8A); the type II isotype was constitutively present and induced to a lesser extent. Induction of arginase was detectable when early AHR developed. The early induction of arginase and AHR precedes leukocyte recruitment (Yang, M. et al., supra). We propose that the induction of AHR by IL-13 may be related to the ability of arginase to functionally inhibit production of the bronchodilator NO by substrate depletion (Morris, S. M., Jr. *Annual Review of Nutrition* 22, 87-105 (2002); Mills, C. D. *Crit Rev Immunol* 21, 399-425 (2001).

Example 12

Lung Arginase Induction in vivo is Primarily STAT6 Dependent

Figure 8B:
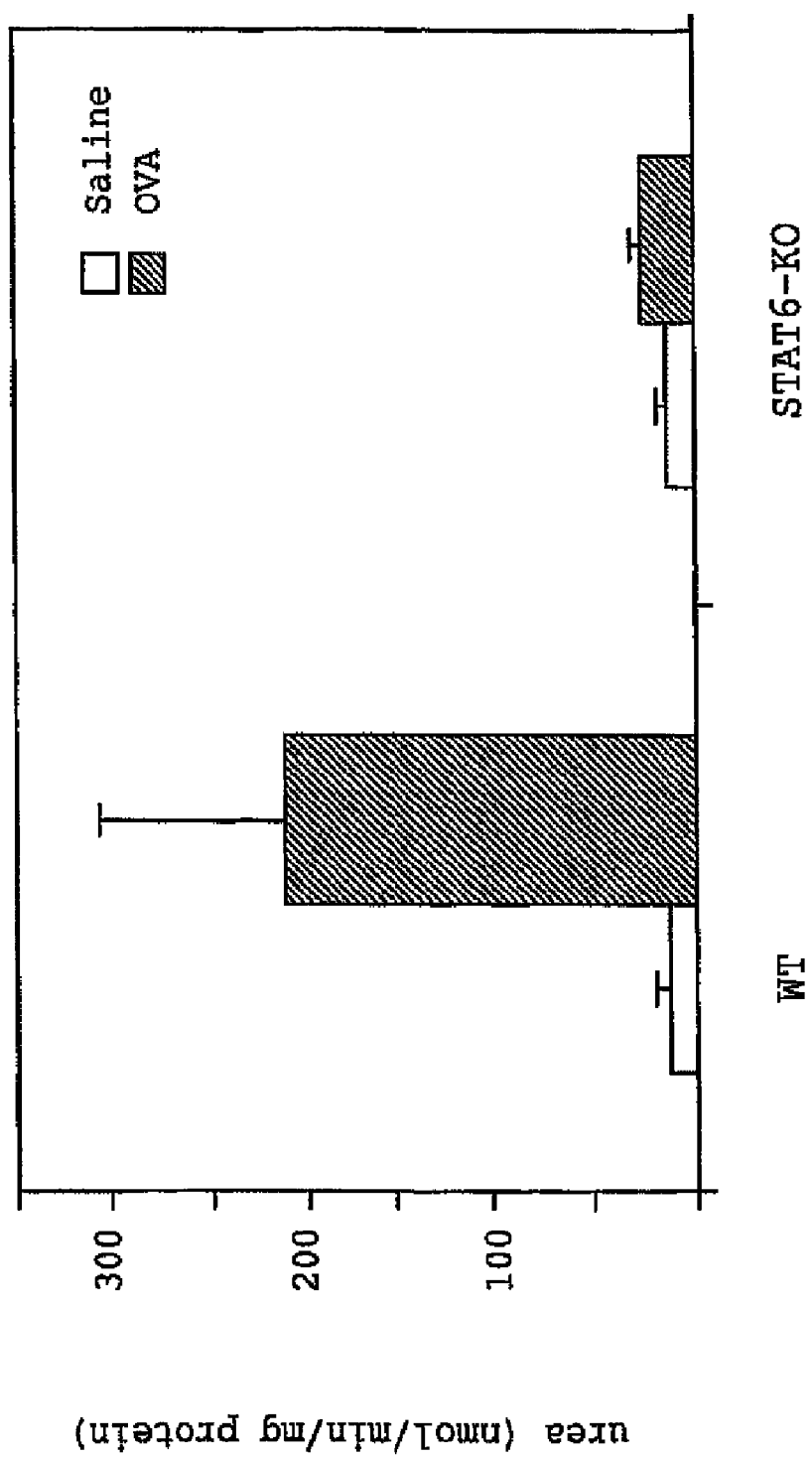
FIG. 8B is a bar graph illustrating arginase activity in the lungs of saline and OVA-challenged wild-type (WT) and STAT6-deficient (STAT6-KO) mice. Arginase activity was measured in lung lysates using the blood urea nitrogen reagent.

IL-4 and IL-13 share similar signaling requirements such as utilization of the IL-4Rα chain and the induction of janus kinase 1 and STAT6. A subset of their responses has been shown to be STAT6 dependent (Shimoda, K. et al. *Nature* 380, 630-3 (1996); Ihle, J. N. *Curr Opin Cell Biol* 13, 211-7 (2001)). In order to test the role of STAT6 in the induction of arginase I in vivo, IL-4 lung transgenic mice that contained wild-type or gene targeted STAT6 were examined. Whereas IL-4 lung transgenic mice contained abundant arginase I mRNA, in the absence of STAT6, there was a complete loss of the IL-4 induced arginase I mRNA. Interestingly, the IL-4 transgene-induced arginase II mRNA signal was only partially attenuated (if at all) in STAT6-deficient mice, indicating that arginase II, in contrast to arginase I, was largely STAT6-independent. These findings support in vitro studies that have demonstrated shared and distinct signaling requirements for these two isoenzymes (Morris, S. M., Jr. Annual Review of Nutrition 22, 87-105 (2002). The next focus of the laboratory was to determine if allergen-induced arginase was dependent upon STAT6. This would determine if allergen induced arginase was predominantly downstream from IL-4 and IL-13 signaling. Notably, mice deficient in STAT6 had a 90% reduction in allergen-induced induced lung arginase activity (FIG. 8B), suggesting that arginase I was the predominant inducible isotype in the asthmatic lung. Taken together, these findings indicate that induction of arginase during allergic lung inflammation is largely downstream from IL-4, IL-13, and STAT6. These results are consistent with the recent finding that IL-4 and IL-13 inhibit NO production in macrophages by a STAT6-dependent pathway (Rutschman, R. et al. J Immunol 166, 2173-7 (2001). Consistent with these findings, the murine arginase I promoter contains a single STAT6 site that is required for response to IL-4 (Morris, S. M., Jr. *Annual Review of Nutrition* 22, 87-105 (2002).

Example 13

Analysis of Human Bronchoalveolar Lavage Cells

Fiberoptic bronchoscopy of allergic asthmatics (not taking glucocorticoids for 12 weeks) and healthy controls following their informed consent was conducted, as previously reported (Olivenstein et al., *J Allergy Clin Immunol* 103, 238-45 (1999). Immunohistochemistry of cytospins (following methanol/acetone fixation) were stained with monoclonal mouse IgGI anti-human arginase I (BD Biosciences) using 1/100 dilution. The slides were developed in Fast Red (Sigma Chemical) in the presence of levamisole, as described in Hamid, Q. Immunohistochemistry. in *Allergy and Allergic Disease*, 1:775-778 (Blackwell Science Ltd, London, 1997). For negative control preparations, the primary antibody was replaced by saline or non-immune mouse IgGI. A minimum of 1000 cells on blindly coded cytospin slides were scored for the number of positive cells, expressed as a percentage of total cells.

Example 14

Determination of Allergy Signature Genes

Mice were sensitizing twice, two weeks apart, with 50 µg of ovalbumin (OVA grade V; SIGMA A-5503) in the presence of 1 mg of the aluminum potassium sulfate adjuvant (alum: $ALK(SO_4)_2-12H_2O$; SIGMA A-7210), by intraperitoneal injection. Before each intragastric challenge, mice were deprived of food for 3 to 4 hours. Three times a week, mice were held in the supine position and orally administered soluble OVA dissolved in 250 µl of 0.9% sterile saline. Challenges were performed with intragastric feeding needles (22G -1.5 in -1.25 mm ball; Fisher 01-290-2B). Diarrhea was assessed by visually monitoring mice for 1 hour following oral allergen challenge.

Following Trizol purification, RNA was repurified with phenol-chloroform extraction and ethanol precipitation. Purified RNA from 4 saline treated and 4 OVA challenged mice (obtained 90 minutes after 10 OVA or saline challenges) were then pooled together and processed at Children's Hospital Medical Center Affymetrix Gene Chip Core facility. Briefly, RNA quality was first assessed using the Agilent bioanalyzer (Agilent Technologies, Palo Alto, Calif.) and only those samples with 28S/18S ratios between 1.3 and 2 were subsequently used. RNA was converted to cDNA with Superscript choice for cDNA synthesis (Invitrogen, Carlsbad, Calif.) and subsequently converted to biotinylated cRNA with Enzo High Yield RNA Transcript labeling kit (Enzo diagnostics, Farmingdale N.Y.).

After hybridization to the murine U74Av2 GeneChip (Affymetrix, Santa Clara, Calif.), the gene chips were automatically washed and stained with streptavidin-phycoerythrin using a fluidics system. The chips were scanned with a Hewlett Packard GeneArray Scanner. From data image files, gene transcript levels were determined using algorithms in the Microarray Analysis Suite Version 4 software (Affymetrix). Two measures of gene expression were used, absolute call and average difference. Absolute call is a qualitative measure in which each gene is assigned a call of present, marginal or absent based on the hybridization of the RNA to the probe set. Average difference is a quantitative measure of the level of gene expression, calculated by taking the difference between mismatch and perfect match of every probe pair and averaging the differences over the entire probe set.

Differences between saline and allergen-treated mice were also determined using the GeneSpring software (Silicon Genetics, Redwood City, Calif.). Data were normalized to the average of the saline-treated mice. Gene lists were created that contained genes with $p<0.05$ and >2-fold change (using genes that received a present call based on the hybridization signal). Subsequently, genes lists between asthma "signature" genes and GI allergy "signature" genes were overlapped to obtain a common set of generalized "allergy" signature genes.

Example 15

Inhibition of Lung Arginase with NOHA in vitro and in vivo

Figure 11A:
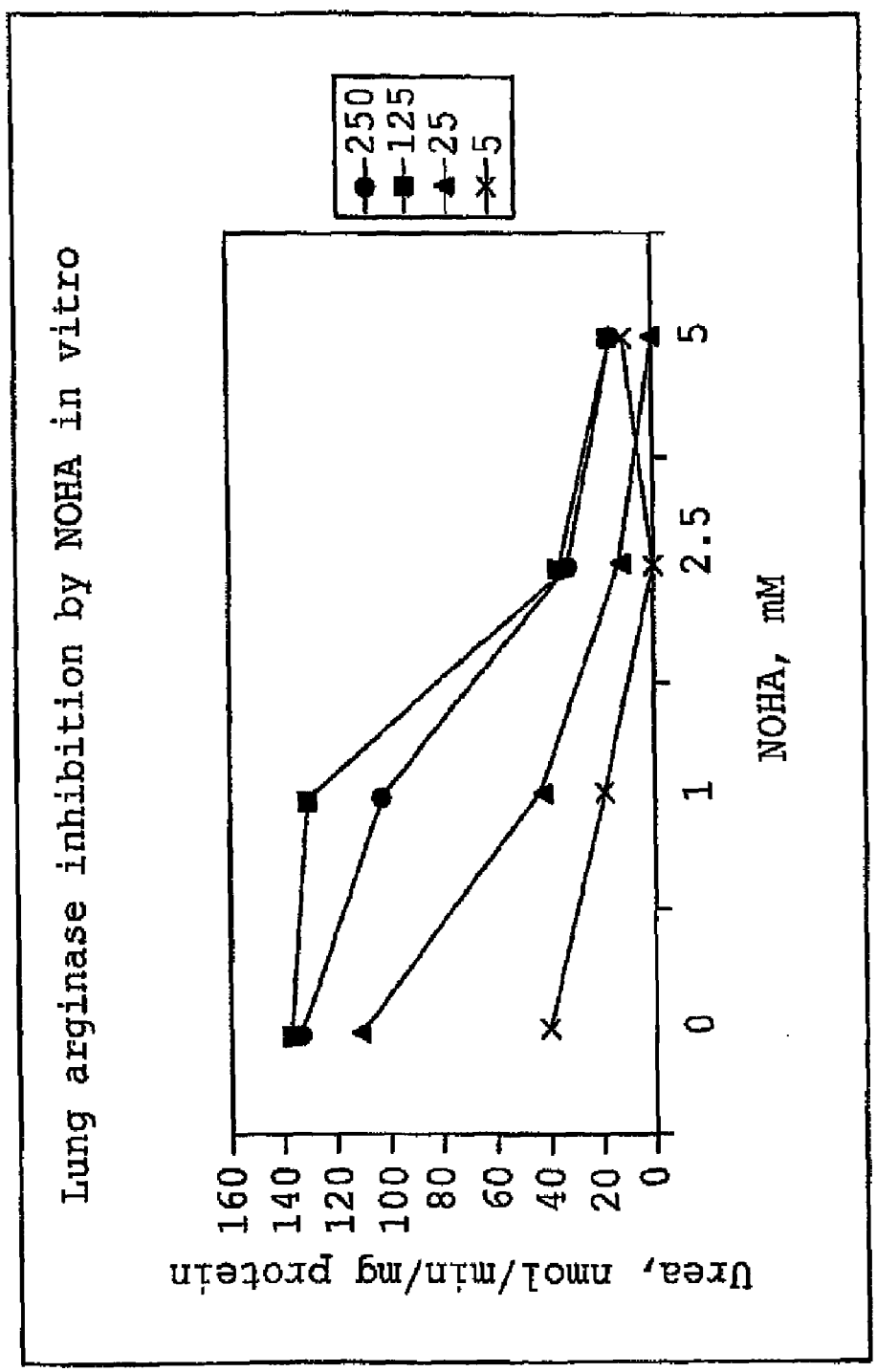
FIGS. 11A and 11B are line graphs showing the results of treating lung lysates with N(omega)-hydroxy-L-arginine (NOHA).
Figure 11B:
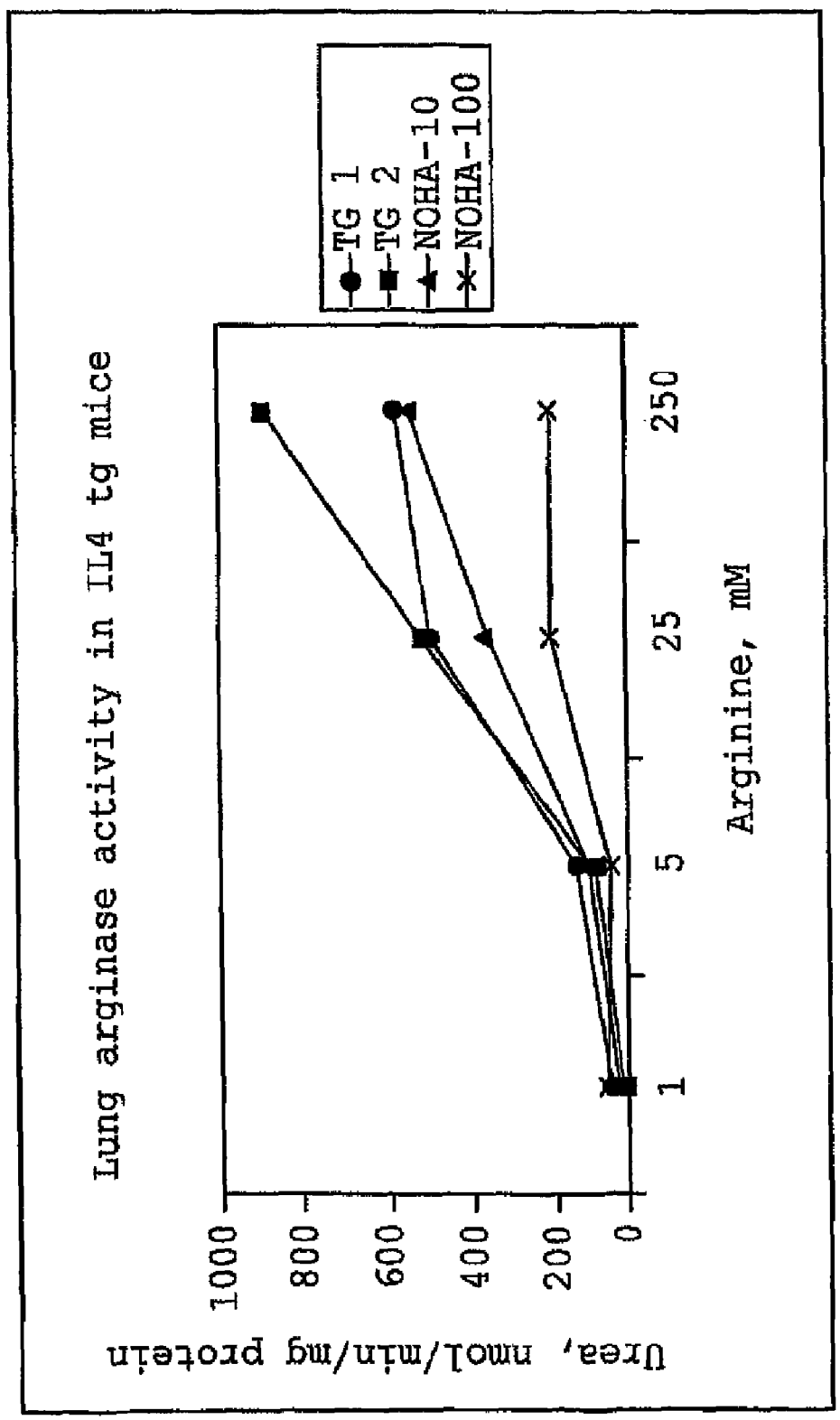

IL-4 lung transgenic mice, which have markedly elevated level of lung arginase mRNA and activity, were used to examine the effect of NOHA in vitro and in vivo (FIG. 11). In FIG. 11A, lung lysates from IL-4 lung transgenic mice were incubated with NOHA and the arginase activity at different doses of NOHA (x axis) and arginine is shown. In FIG. 11B, IL-4 transgenic mice were treated with intratracheal NOHA (two doses: 10 and 100 mcg) and the arginase activity in the lungs was measured 4 hrs later. As indicated, NOHA was effective to reduce arginase activity in lung lysates and when given intratracheally to IL-4 transgenic mice.

Example 16

Treatment of Individual with Anti-Arginase Compound

An individual suffering from asthma is identified. The individual is provided with a therapeutically effective amount of N(omega)-hydroxy-L-arginine to reduce the indications of asthma. Following inhalation of the compound the individual's asthma symptoms are reduced.

Example 17

Additional Compounds that Regulate Arginase Down-stream Products

Difluoromethylornithine (DFMO) is an inhibitor of ODC and is expected to be a useful treatment for inhibiting asthma or allergy. Other potentially useful compounds include but are not limited to N(omega)-hydroxy-L-arginine and boronic acid based transition state analogues such as 2(S)-amino-6-boronohexanoic acid (ABH) and S-(2-boronoethyl)-L-cysteine (BEC), which may inhibit asthma symptoms. Other inhibitors are described by Que, et al. (Nitric Oxide. 2002 February; 6(1):1-8).

Example 18

Effect of the Arginase Pathway Inhibitor DFMO on Immunopathogenesis

A blockade in the arginase pathway that is downstream of arginase action may have an important effect on experimental asthma in mice. DFMO is an irreversible inhibitor that blocks ornithine decarboxylase (ODC) action, the biochemical step that catalyzes the synthesis of putrescine from the precursor molecule ornithine. DFMO is a commercially available drug (Sigma and llex Oncology, Inc) that has been well studied in multiple species including mice (Prakash, et al (1978) *Cancer Res* 38:3059-3062; Meyskens and Gerner (1999) *Clin. Cancer Res* 5:945-951).

Example 19

Effect of the Administration of the Arginase Pathway Inhibitor DFMO After Asthma Induction in the Experimental Murine Asthma Model Agents that block arginase pathways in the lung may be useful to alleviate or reduce the effects of asthma once it has established itself in the lung of the patient. To determine whether blocking the arginase pathway has any effect, the exemplary inhibitor of arginase pathway activity, DFMO, is administered to a patient by conventional means. It is discovered that the patients receiving DFMO show lower effects of asthma as compared to patients treated with saline.

Example 20

Effect of the Administration of the Arginase I Inhibitor NOHA on the Development of Allergen-Induced Airway Hyperresponsiveness Airway reactivity to methacholine was assessed in conscious, unrestrained mice by barometric plethysmography, using apparatus and software supplied by Buxco (Troy, N.Y.). This system yields a dimensionless parameter known as enhanced pause (Penh), reflecting changes in wave-form of the pressure signal from the plethysmography chamber combined with a timing comparison of early and late expiration, which can be used to empirically monitor airway function. Measurement was performed as previously described in Yang, M. et al. (*Am J Respir Cell Mol Biol* 25, 522-30 (2001) and Hamelmann, E. et al. *American Journal of Respiratory & Critical Care Medicine* 156, 766-75 (1997).

Briefly, mice were placed in the chamber and baseline reading taken and averaged for 3 minutes. Aerosolized methacholine (concentrations in solution ranging from 3.125 to 50 mg/ml) was then delivered through an inlet into the chamber for 2 min and readings averaged over a period of 3 min after each dose was administered.

Figure 12:
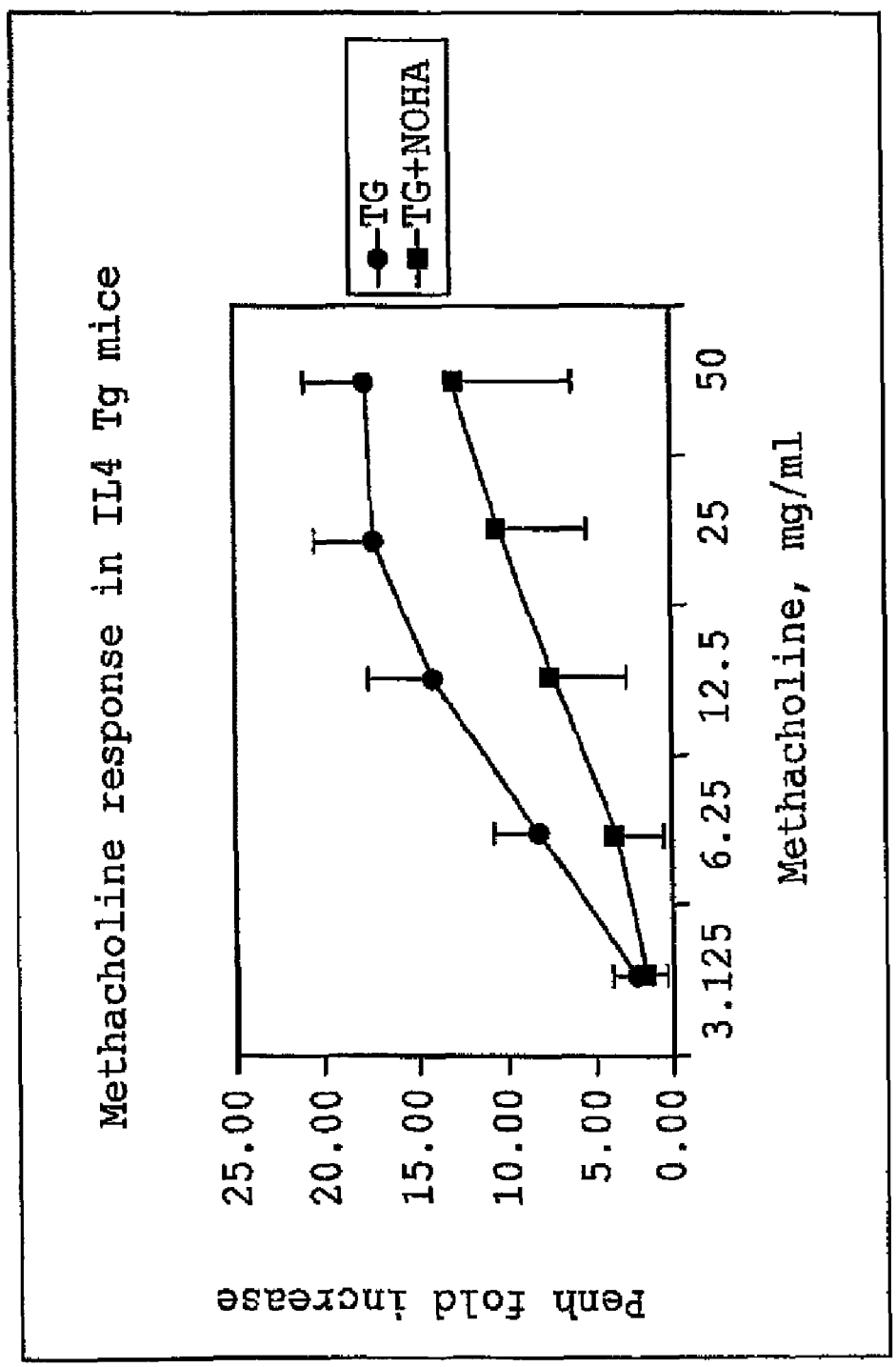
FIG. 12 is a line graph showing the results of airway hyperreactivity measurements (recorded as Penh) in asthmatic mice (IL4/IL5 bitransgenic lung mice) treated with intratracheal NOHA.

To study the effect of NOHA, IL-4/IL-5 transgenic lungs (that have increased airway hyperresponsiveness as measured by Penh) were exposed to intratracheal NOHA (100 mcg) and Penh measurements were recorded 4 hrs later (FIG. 12). As a control, the value of Penh in untreated IL4/IL5 lung transgenic mice is shown.

While the present invention, including preferred embodiments, has been described fully and completely herein, it is to be understood that modifications will occur to those skilled in the art without departing from the spirit of the invention. Thus, although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims and any equivalents thereof All documents cited herein are incorporated herein by reference in their entireties.

What is claimed is:

1. A method of detecting the presence of asthma or allergies in a patient comprising:
    measuring the expression level of full length CAT2, arginase I, or arginase II mRNA from said patient; and
    comparing said measurement to a measurement obtained from a control individual, wherein a patient exhibiting higher levels of said CAT2, arginase I, or arginase II mRNA as compared to the control individual is determined to have asthma or allergies.

2. The method of claim 1, wherein said patient is a human.

3. The method of claim 1, wherein said measurement is performed using a biological fluid sample from the respiratory tract of said patient.

4. The method of claim 1, wherein measurement is performed using a microarray assay.

5. The method of claim 1, wherein said measurement is performed using a Northern blot assay.

6. The method of claim 1, wherein the threshold for said higher level is an expression level 2-fold higher than the expression level in said control individuals.

7. The method of claim 1, wherein said method is used to detect the presence of asthma.

8. The method of claim 1, wherein said method is used to detect the presence of allergy.

9. The method of claim 1, wherein the expression level of full length CAT2mRNA is measured.

10. The method of claim 1, wherein the expression level of full length arginase I mRNA is measured.

11. The method of claim 1, wherein the expression level of full length arginase II mRNA is measured.

12. A method of detecting the presence of asthma or allergies in a patient comprising:
    measuring the expression level of a full length mRNA from at least one gene encoding a protein that decreases the level of arginine in said patient; and
    comparing said measurement to a measurement obtained from a control individual, wherein a patient exhibiting higher levels of said mRNA as compared to the control individual is determined to have asthma or allergies.

13. The method of claim 12, wherein said at least one gene is selected from the group consisting of: CAT2, arginase I, and arginase II.

14. The method of claim 12, wherein said patient is a human.

15. The method of claim 12, wherein said measurement is performed using a biological fluid sample from the respiratory tract of said patient.

16. The method of claim 1, wherein measurement is performed using a microarray assay.

17. The method of claim 12, wherein the threshold for said higher level is an expression level 2-fold higher than the expression level in said control individuals.

18. The method of claim 12, wherein said method is used to detect the presence of asthma.

19. The method of claim 12, wherein said method is used to detect the presence of allergy.

* * * * *